US009493383B2

(12) United States Patent
Kim et al.

(10) Patent No.: US 9,493,383 B2
(45) Date of Patent: Nov. 15, 2016

(54) ORGANIC COMPOUND AND ORGANIC LIGHT EMITTING DEVICE USING THE SAME

(71) Applicants: Kong Kyeom Kim, Daejeon (KR); Sung Kil Hong, Daejeon (KR); Hye Young Jang, Daejeon (KR); Dong Seob Jeong, Daejeon (KR)

(72) Inventors: Kong Kyeom Kim, Daejeon (KR); Sung Kil Hong, Daejeon (KR); Hye Young Jang, Daejeon (KR); Dong Seob Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 703 days.

(21) Appl. No.: 13/623,686

(22) Filed: Sep. 20, 2012

(65) Prior Publication Data

US 2014/0077165 A1 Mar. 20, 2014

Related U.S. Application Data

(62) Division of application No. 11/520,746, filed on Sep. 14, 2006, now Pat. No. 8,298,683.

(30) Foreign Application Priority Data

Sep. 15, 2005 (KR) .................. 10-2005-0086501

(51) Int. Cl.
*C07C 13/64* (2006.01)
*C07C 211/61* (2006.01)
(Continued)

(52) U.S. Cl.
CPC ............... *C07C 13/64* (2013.01); *C07C 13/58* (2013.01); *C07C 211/61* (2013.01);
(Continued)

(58) Field of Classification Search
CPC ... C07C 13/58; C07C 13/64; C07C 2102/10; C07C 2103/24; C07C 211/61; C07D 209/82; C07D 209/86; C07D 235/18; C09K 11/06; C09K 2211/1007; C09K 2211/1011; C09K 2211/1014; C09K 2211/1029; H01L 2251/308; H01L 51/005; H01L 51/0064; H05B 33/14

See application file for complete search history.

(56) References Cited

U.S. PATENT DOCUMENTS

| 5,968,675 A | 10/1999 | Tamano et al. |
| 6,465,115 B2 | 10/2002 | Shi et al. |

(Continued)

FOREIGN PATENT DOCUMENTS

| EP | 1888707 | 2/2008 |
| JP | 1996087122 A | 4/1996 |

(Continued)

OTHER PUBLICATIONS

Translation for JP 2005-008600 (publication date: Jan. 2005).*

(Continued)

*Primary Examiner* — Dawn Garrett
(74) *Attorney, Agent, or Firm* — Dentons US LLP

(57) ABSTRACT

The present invention provides an organic light emitting device comprising a first electrode, at least one organic layer and a second electrode, laminated successively, in which at least one layer of the organic layer has a polycyclic aromatic hydrocarbon as a core and comprises at least one of a derivative in which a substituted or unsubstituted $C_{2-30}$ cycloalkane, or a substituted or unsubstituted $C_{5-50}$ polycycloalkane is directly fused to the core or fused to a substituent of the core; and a new organic compound usable in the organic light emitting device. Furthermore, the present invention provides a charge carrier extracting, injecting or transporting material which has a polycyclic aromatic hydrocarbon as a core and comprises a derivative in which a substituted or unsubstituted $C_{2-30}$ cycloalkane, or a substituted or unsubstituted $C_{5-50}$ polycycloalkane is directly fused to the core or fused to a substituent of the core.

4 Claims, 2 Drawing Sheets

(51) Int. Cl.
C07D 209/86 (2006.01)
H01L 51/00 (2006.01)
C07D 209/82 (2006.01)
C07D 235/18 (2006.01)
C07C 13/58 (2006.01)
C09K 11/06 (2006.01)
H05B 33/14 (2006.01)

(52) U.S. Cl.
CPC ......... C07D 209/82 (2013.01); C07D 209/86 (2013.01); C07D 235/18 (2013.01); C09K 11/06 (2013.01); H01L 51/005 (2013.01); H01L 51/0058 (2013.01); H05B 33/14 (2013.01); C07C 2102/10 (2013.01); C07C 2103/24 (2013.01); C09K 2211/1007 (2013.01); C09K 2211/1011 (2013.01); C09K 2211/1014 (2013.01); C09K 2211/1029 (2013.01); H01L 51/0064 (2013.01); H01L 2251/308 (2013.01)

(56) References Cited

U.S. PATENT DOCUMENTS

| | | | |
|---|---|---|---|
| 7,067,179 B1 | 6/2006 | Ogawa et al. | |
| 7,471,041 B2 | 12/2008 | Spindler | |
| 8,298,683 B2* | 10/2012 | Kim | C07C 13/62 136/263 |
| 8,679,645 B2* | 3/2014 | Heil et al. | 428/690 |
| 2005/0014795 A1 | 1/2005 | Baroni et al. | |
| 2006/0154076 A1 | 7/2006 | Kubota et al. | |
| 2007/0009760 A1 | 1/2007 | Inoue et al. | |
| 2007/0059556 A1* | 3/2007 | Kim et al. | 428/690 |
| 2008/0166593 A1* | 7/2008 | Stoessel | C09K 11/06 428/704 |
| 2009/0128009 A1 | 5/2009 | Heil et al. | |

FOREIGN PATENT DOCUMENTS

| | | |
|---|---|---|
| JP | 1997301899 A | 11/1997 |
| JP | 11-273860 | 10/1999 |
| JP | 1999273860 A | 10/1999 |
| JP | 2004-059535 A | 2/2004 |
| JP | 2005/8600 | 1/2005 |
| JP | 2005-008600 A | 1/2005 |
| JP | 2005505621 A | 2/2005 |
| JP | 2008-545762 A | 12/2008 |
| WO | 0110803 A1 | 2/2001 |
| WO | WO 2004/083160 | 9/2004 |
| WO | WO 2005/033118 | 4/2005 |
| WO | WO 2005/05528 | 6/2005 |
| WO | 2005121057 A1 | 12/2005 |
| WO | 2006131192 A1 | 12/2006 |

OTHER PUBLICATIONS

Tsutsui, et al. "Charge recombination electroluminescence in organic thin-film devices without charge injection from external electrodes"; 2004 American Institute of Physics, vol. 85, No. 12.
Matsuura, et al. "Synthesis and Electronic Properties of Anthracene Fully Annelated with Bicyclo[2.2.2] octene Frameworks"; Tetrahedron Letters, vol. 38, No. 19, pp. 3427-3430, 1997.
Rathore, et al. "Novel Synthesis and Structures of Tris-Annelated Benzene Donors for the Electron-Density Elucidation of the Classical-Mills-Nixon Effect"; J. Am. Chem. Soc. 1998, 120, 6012-6018; 1998 American Chemical Society.
Cason et all, "The Synthesis of 1, 9-Dimethyl-1, 2-Benzanthracene", Journal of Organic Chemistry, vol. 17, No. 2, Feb. 29, 1952, pp. 298-312.
Lepage et al. "1,4,5,8,9,10-Hexaphenylanthracene", Bulletin De La Societe Chimique De France, No. 8, Jan. 1, 1965, pp. 2342-2344, XP008134080.
Berichte der Deutschen Chemischen Gesellschaft, 1929, vol. 62, p. 2337-2372.
Bulletin de la Societe Chimique de France, 1946, p. 106-109.
Chemistry Physics, 1993, vol. 176, p. 321-336.
Chemistry-A European Journal, 2003, vol. 9, p. 5036-5047.
Chemistry-A European Journal, 2006, vol. 12, p. 1629-1641.
European Journal of Organic Chemistry, 2002, p. 4024-4031.
Helvetica Chimica Acta, 1975, vol. 58, p. 380-397.
Helvetica Chimica Acta, 1975, vol. 58, p. 397-415.
Journal of Organic Chemistry, 1967, vol. 32, p. 1304-1307.
Journal of Organic Chemistry, 1984, vol. 49, p. 304-310.
Journal of Organic Chemistry, 1997, vol. 62, p. 2381-2386.
Journal of Physical Chemistry A, 1999, vol. 103, p. 9167-9173.
Journal of Physical Chemistry, 1994, vol. 98, p. 9750-9763.
Journal of Physical Chemistry, 1995, vol. 99, p. 14223-14230.
Journal of the American Chemical Society, 1974, vol. 96, No. 7, p. 2270-2271.
Journal of the American Chemical Society, 1978, vol. 100, No. 16, p. 4964-4968.
Journal of the American Chemical Society, 2002, vol. 124, p. 10171-10181.
Journal of the American Chemical Society, 2005, vol. 127, p. 10162-10163.
Photochemical & Photobiological Sciences, 2004, vol. 3, No. 11-12, p. 1047-1051.
J. Chem. Soc. Perkin Trans. 2, 1996, No. 4, p. 639-648.
Acta Cryst., 2005, E61, p. o1869-o1871.
Tetrahedron Letters, 1985, vol. 26, No. 22, p. 2613-2616.
Tetrahedron Letters, 1993, vol. 34, No. 21, p. 3397-3400.
Tetrahedron Letters, 1997, vol. 38, No. 10, p. 1745-1748.
Tetrahedron Letters, 2002, vol. 43, p. 4963-4968.
Tetrahedron, 1992, vol. 48, No. 36, p. 7663-7678.
Journal of the American Chemical Society, 1940, 62, p. 2408-2412.
Office Action of Japanese Patent Office in Appl'n. No. 2008-531020, dated Jun. 25, 2013.
Office Action of European Patent Office in Appl'n. No. 11 154 963.0, dated Oct. 24, 2012.
Office Action of European Patent Office in Appl'n. No. 11 154 964.8, dated Nov. 12, 2012.

* cited by examiner

ORGANIC COMPOUND AND ORGANIC LIGHT EMITTING DEVICE USING THE SAME

This application is a Divisional of U.S. patent application Ser. No. 11/520,746, filed Sep. 14, 2006, which claims priority to Korean Patent Application No. 10-2005-0086501, filed on Sep. 15, 2005, all of which are hereby incorporated by reference in their entirety.

TECHNICAL FIELD

The present invention relates to a new compound usable in an organic layer of an organic light emitting device and an organic light emitting device using the same.

BACKGROUND ART

In general, the term "organic light emitting phenomenon" refers to a phenomenon in which electric energy is converted to light energy by means of an organic material. Particularly, when an organic layer is disposed between an anode and a cathode and then a voltage is applied between both electrodes, holes from the anode and electrons from a cathode are injected into the organic layer, the holes and the electrons injected are combined together to form excitons. Further, when the excitons drop to a ground state, lights are emitted.

In addition to the above-described organic light emitting phenomenon in which light emission is made by recombining of charges injected from both electrodes, there is another mechanism in which holes and electrons are not injected from external electrodes but are generated by an amphoteric charge-generating layer under the application of alternating current voltage, as in the case of an inorganic thin film light emitting device, and the holes and electrons move to an organic thin film layer, resulting in light emission (Appl. Phys. Lett., 85(12), 2382-2384).

Since Pope, Kallman and Magnate have found electroluminescence in anthracene single crystal in 1963, active research and development into OLEDs (Organic Light Emitting Devices) have been made up to now. Recently, organic light emitting devices have been used in various applied products such as flat panel display devices and lighting devices.

In order to manufacture more efficient organic light emitting devices, an attempt has been made to manufacture an organic layer in the device in the form of a multilayer structure instead of a monolayer structure. Most of currently used organic light emitting devices have a structure in which an organic layer and electrodes are deposited. The organic layer generally has a multilayer structure including a hole injecting layer, a hole transporting layer, a light emitting layer, an electron transporting layer and an electron injecting layer.

It is known that organic light emitting devices are characterized by high brightness, high efficiency, low drive voltage, color changeability, low cost, etc. However, in order to meet such characteristics, each layer forming an organic layer in a device (for example, a hole injecting layer, a hole transporting layer, a light emitting layer, an electron transporting layer and an electron injecting layer) must be formed of more stable and efficient materials.

DISCLOSURE

Technical Problem

The present inventors have attempted molecular design to solve problems caused by the intermolecular interaction of polycyclic aromatic hydrocarbon derivatives such as anthracene, naphthalene, pyrene, rubrene and perylene, which is capable of carrying out hole transportation, light emission and/or electron transportation in an organic light emitting device.

Technical Solution

Accordingly, it is an object of the present invention to provide a new organic compound having a structure in which at least one cycloalkane or polycycloalkane is directly linked to a polycyclic aromatic hydrocarbon as a core or is linked to a substituent thereof.

Advantageous Effects

According to the invention, a derivative having a structure in which at least one cycloalkane or polycycloalkane is directly fused to a polycyclic aromatic hydrocarbon as a core or is fused to a substituent of the polycyclic aromatic hydrocarbon, can maximally decrease interaction between compounds by bulky cycloalkane or polycycloalkane moieties (steric protection), and can further exhibit induction effect and hyperconjugative effect.

Therefore, it is possible to efficiently exhibit a light-emitting color having a low reduction in light emitting efficiency and having high color purity due to a reduction in the interaction between compounds and it is also possible to enhance the life span, the efficiency and the thermal stability of a device and to drive it at low voltage when the compound according to the invention is used in an organic light emitting device.

[Reference numerals]

Figure 1:
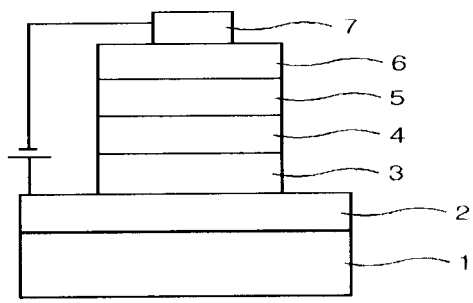
FIGS. 1 to 5 are cross-sectional views illustrating a structure of a general organic light emitting device usable in the present invention.

| | |
|---|---|
| 1: substrate | 2: anode |
| 3: hole injecting layer | 4: hole transporting layer |
| 5: organic light emitting layer | 6: electron transporting layer |
| 7: cathode | |

BEST MODE

The present invention provides an organic light emitting device comprising a first electrode, at least one organic layer, and a second electrode, laminated successively, in which at least one layer of the organic layer has a polycyclic aromatic hydrocarbon as a core and comprises at least one of a derivative in which a substituted or unsubstituted $C_{2-30}$ cycloalkane, or a substituted or unsubstituted $C_{5-50}$ polycycloalkane is directly fused to the core.

Further, the present invention provides an organic light emitting device comprising a first electrode, at least one organic layer, and a second electrode, laminated successively, in which at least one layer of the organic layer has a polycyclic aromatic hydrocarbon as a core and comprises at least one of a derivative in which a substituted or unsubstituted $C_{2-30}$ cycloalkane, or a substituted or unsubstituted $C_{5-50}$ polycycloalkane is fused to a substituent of the polycyclic aromatic hydrocarbon as the core.

Furthermore, the present invention provides a charge carrier extracting, injecting or transporting material which has a polycyclic aromatic hydrocarbon as a core and comprises a derivative in which a substituted or unsubstituted $C_{2-30}$ cycloalkane, or a substituted or unsubstituted $C_{5-50}$ polycycloalkane is directly fused to the core or fused to a substituent of the core.

Still furthermore, the present invention provides a compound of the following formula (1), a compound of the following formula (2) and a compound of the following formula (3), which are capable of carrying out at least one function of a light emitting material, a hole transporting material and an electron transporting material:

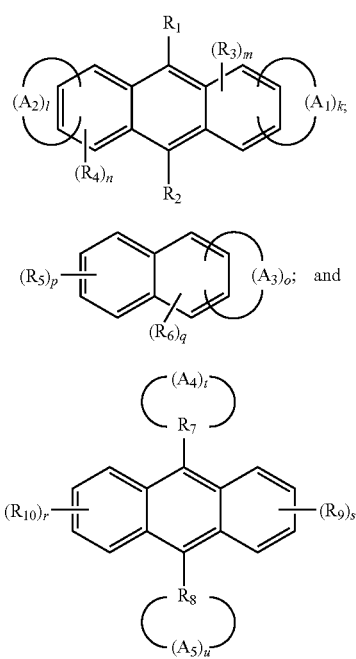

wherein

means a substituted or unsubstituted $C_{2-30}$ cycloalkane, or a substituted or unsubstituted $C_{5-50}$ polycycloalkane directly fused to a benzene ring of a polycyclic aromatic hydrocarbon (wherein A' means $A_1$, $A_2$ and $A_3$);

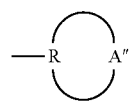

means a substituted or unsubstituted $C_{2-30}$ cycloalkane, or a substituted or unsubstituted $C_{5-50}$ polycycloalkane fused to a substituent of a polycyclic aromatic hydrocarbon (wherein R means $R_7$ and $R_8$; and A" means $A_4$ and $A_5$). In this case, the benzene ring is contained in the substituent moiety of the polycyclic aromatic hydrocarbon to which cycloalkane or polycycloalkane is fused; and the substituents $R_1$ to $R_{10}$ are the same or different from each other and are each selected from the group consisting of a hydrogen, a halogen, a nitrile group (—CN), a nitro group (—NO$_2$), a sulfonyl group (—SO$_2$R'), a sulfoxide group (—SOR'), a sulfonamide group (—SO$_2$NR'$_2$), a sulfonate group (—SO$_3$R), a trifluoromethyl group (—CF$_3$), an ester group (—COOR'), an amide group (—CONHR' or —CONR'R"), a substituted or unsubstituted and linear or branched $C_{1-12}$ alkoxy group, a substituted or unsubstituted and linear or branched $C_{1-20}$ aliphatic hydrocarbon group, a substituted or unsubstituted and aromatic or nonaromatic heterocyclic group, a substituted or unsubstituted aryl group, a substituted or unsubstituted and mono- or diarylamine group and a substituted or unsubstituted aralkylamine group, two R's may form a fused ring, or two R's may linearly linked to each other to form a polycyclic aromatic hydrocarbon derivative as a polymer, provided that $R_1$ and $R_2$ are not simultaneously a hydrogen atom.

In this case, R' and R" are each selected from the group consisting of a substituted or unsubstituted $C_{1-60}$ alkyl group, a substituted or unsubstituted aryl group and a substituted or unsubstituted 5-7 membered heterocyclic group.

In R' and R", the $C_{1-60}$ alkyl group, the aryl group and the heterocyclic group each may be substituted with one or more optional group selected from one or more amine group, an amide group, an ether group and an ester group.

In the formula, the aryl group may be selected from the group consisting of a phenyl group, a biphenyl group, a terphenyl group, a benzyl group, a naphthyl group, an anthracenyl group, a tetracenyl group, a pentacenyl group, a perylenyl group and a coronenyl group and these may be monosubstituted, polysubstituted or unsubstituted.

In this case, when the substituent is a substituted aryl group, particularly a substituted phenyl group, it may contain a double bond or triple bond.

Examples of the substituted aryl group include a stilbenzyl group of

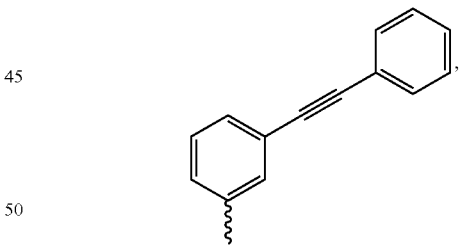

and an acetylenyl group of

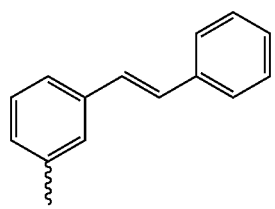

and the substituted aryl group is preferably substituted at the 9-position of an anthracene core.

Examples of the aromatic heterocyclic group in the formula include groups derived from thiophene, furan, pyrrole, imidazole, thiazole, oxazole, oxadiazole, thiadiazole, triazole, pyridine, pyridazine, pyrazine, quinoline and isoquinoline.

Examples of the $C_{1-20}$ aliphatic hydrocarbon group in the formula include an alkyl group such as a methyl group, an ethyl group, n-propyl group, an isopropyl group, n-butyl group, a sec-butyl group, an isobutyl group, a tert-butyl group, a pentyl group, a hexyl group; an alkenyl group having a double bond, such as a styryl group; and an alkynyl group having a triple bond, such as an acetylene group.

In the formula (1), k and l are an integer of 0, 1 or 2 (provided that $k+l \geq 1$); and m and n are an integer of 1 to 4.

In the formula (2), o is an integer of 1 or 2; and p and q are an integer of 1 to 4.

In the formula (3), r and s are an integer of 1 to 4; and t and u are an integer of 0 to 2, provided that $t+u \geq 1$.

In the case that k, l, o, p, q, r, s, t and u are an integer of 2 or more, there are substituted at several positions of the aromatic ring with not only same substituents but also different substituents.

Unrestricted examples of substituents for the substituted cycloalkane or substituted bicycloalkane include a $C_{1-6}$ alkyl group.

Mode for Invention

Hereinafter, the present invention will be described in more detail.

Polycyclic aromatic hydrocarbons such as anthracene, naphthalene, pyrene, rubrene and perylene can a function as a chromophore. In particular, an organic compound having anthracene as a core is widely used for a hole transporting material, a light emitting material (including a dopant), an electron transporting material, etc. in an organic electronic device such as an organic light emitting device.

As illustrated in the formulae (1), (2) and (3), the present invention is characterized by providing a derivative that has as a core the polycyclic aromatic hydrocarbon such as anthracene, naphthalene, pyrene, rubrene and perylene, in which sterically bulky cycloalkane or polycycloalkane is directly fused to the core or is fused to a substituent of the core.

In the invention, polycycloalkane is preferably bicycloalkane.

According to the invention, the derivative that has the polycyclic aromatic hydrocarbon as a core, in which a substituted or unsubstituted $C_{2-30}$ cycloalkane, or a substituted or unsubstituted $C_{5-50}$ polycycloalkane is directly fused to the core or is fused to a substituent of the core, can be used as a light emitting material and as a light emitting host or a light emitting dopant in an organic light emitting device. In particular, the polycyclic aromatic hydrocarbon derivative according to the invention can emit blue, green and red light by controlling the substituents introduced or the conjugation length.

Examples of the polycyclic aromatic hydrocarbon derivative according to the invention include compounds of the formulae (1) to (3).

The polycyclic aromatic hydrocarbon derivative according to the invention performs light absorption or light emission, thereby determining its main wavelength band.

On the other hand, a substituted or unsubstituted $C_{2-30}$ cycloalkane, or a substituted or unsubstituted $C_{5-50}$ bicycloalkane directly fused to the polycyclic aromatic hydrocarbon core can move the wavelength of the chromophore to a longer wavelength.

Since anthracene itself has amphoteric properties, holes or electrons can be selectively transported depending on the introduction of the substituents.

The cycloalkane or polycycloalkane fused to the polycyclic aromatic hydrocarbon can give a nonplanar structure (e.g., chair type) similar to an independent cycloalkane or polycycloalkane to the polycyclic aromatic hydrocarbon, unlike a flat aromatic ring. Therefore, by further exhibiting amorphous characteristics, a device can be prevented from breakdown that occurs due to crystallization caused by Joule heat generated upon operation of an organic electronic device such as an organic light emitting device.

Further, since the cycloalkane or polycycloalkane fused to the polycyclic aromatic hydrocarbon is relatively sterically bulky, a melting point and a glass transition temperature of the compound can be increased; the compound has a strong molecular structure and thus has high quantum efficiency; and quenching effects and adverse effects generated by the intermolecular interaction, such as deterioration in color purity caused by the broad light emission band, can be reduced to enhance characteristics of the molecule itself, by subjecting to a steric hindrance due to a bulky molecular structure. Further, the polycyclic aromatic hydrocarbon can improve a function as a dopant capable of inhibiting the intermolecular interaction between the hosts by the introduction of sterically bulky cycloalkane or polycycloalkane into a molecule.

In particular, in a structure in which the aromatic core is surrounded by cycloalkane or polycycloalkane framework, the electronic density of the aromatic core is varied due to an inductive effect and hyperconjugative effect of the cycloalkane or polycycloalkane framework, thereby greatly stabilizing cation radicals. Specifically, the polycyclic aromatic hydrocarbon has p-type behavior stronger than that of the core itself because of the cycloalkane or polycycloalkane framework. Further, from electrochemical oxidation measurements, it can be confirmed that the more the number of cycloalkane or polycycloalkane framework, the easier the oxidation and the more stable the cation radical (see J. Am. Chem. Soc. 1998, 120, 6012-6018 and Tetrahedran Letters (1997), 38 (19), 3427-3430).

Therefore, the polycyclic aromatic hydrocarbon to which the cycloalkane or polycycloalkane is directly fused can be used as a hole transporting material. Unlike an anthracene derivative disclosed in U.S. Pat. No. 6,465,115, a structure surrounded by cycloalkane or polycycloalkane is more electrochemically stable (cationic radical) and the energy level (HOMO) thereof can be optimized. Therefore, the polycyclic aromatic hydrocarbon is improved in stability as the hole transporting material to thus attain a stable morphology and to facilitate hole injection.

The number of the cycloalkane or polycycloalkane fused to the polycyclic aromatic hydrocarbon is preferably 1 to 4.

The cycloalkane fused according to the invention has 2 to 30, preferably 3 to 8 carbon atoms.

The polycycloalkane fused according to the invention has 5 to 50, preferably 5 to 25 carbon atoms.

The polycyclic aromatic hydrocarbon as the core in the invention may be a derivative that is substituted with at least one substituent (R) such as R1 to R6, R9 and R10 described in the formulae (1) to (3).

On the other hand, when the substituted or unsubstituted $C_{2-30}$ cycloalkane, or substituted or unsubstituted $C_{5-50}$ polycycloalkane is fused to the substituent of the core of the polycyclic aromatic hydrocarbon, a benzene ring is preferably contained in the substituent moieties fused.

Specific examples of the compound represented by the formula (1) include, but are not limited to, the compounds represented by the following formulae (1-1) to (1-13):

(1-1)
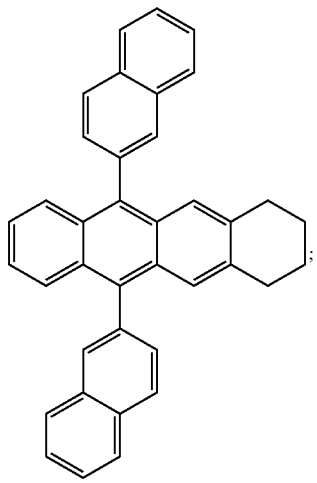

(1-2)
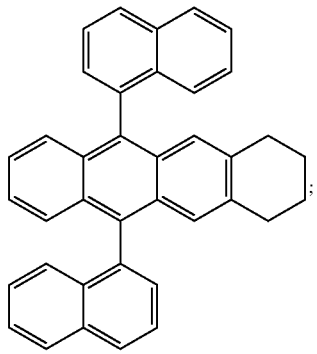

(1-3)
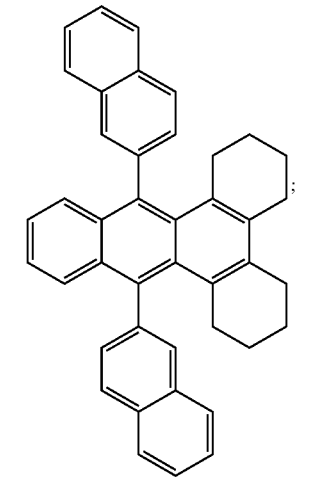

(1-4)
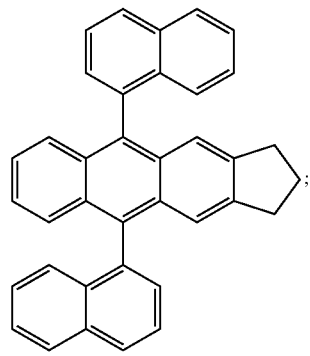

(1-5)
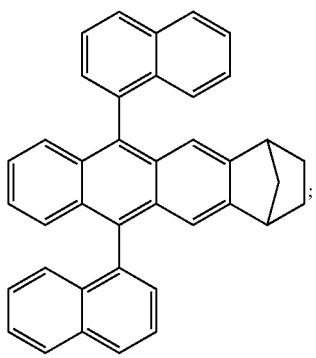

(1-6)
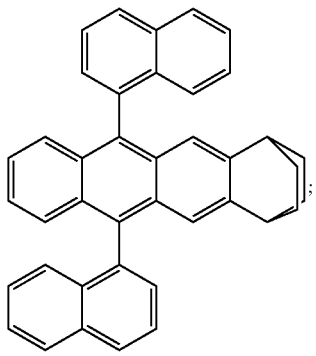

(1-7)
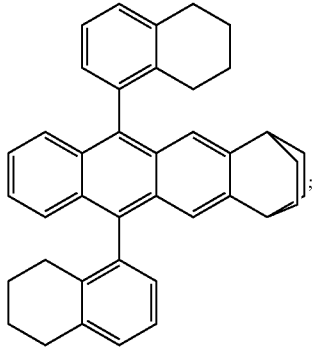

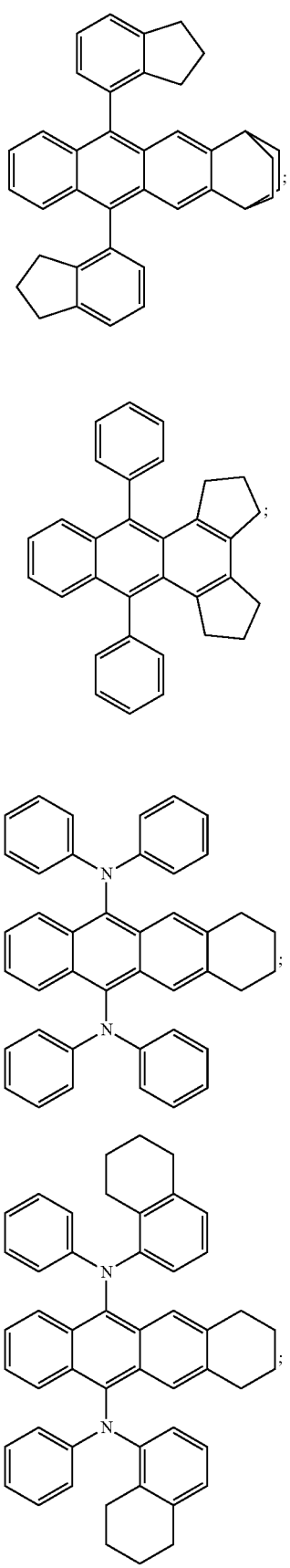

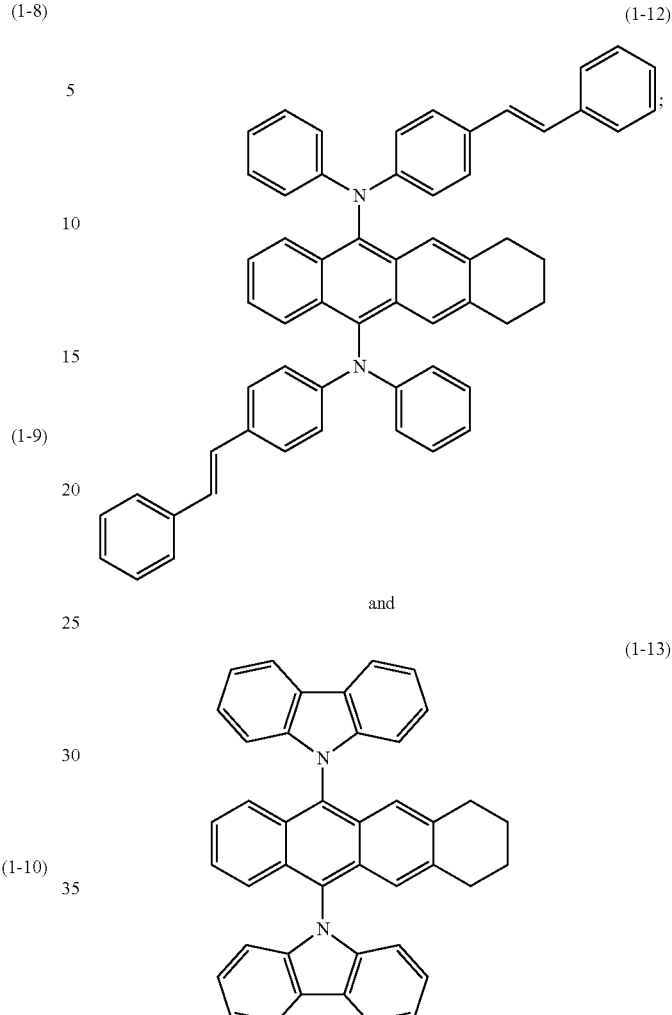

and

In an example of the general production method of the compound of the formula (1), an anthraquinone derivative can be synthesized and reduced to anthracene by a general reduction reaction anthracene, and various substituents can be introduced into a general chemical reaction through a halogenation reaction including bromination at the 9- or 10-position of anthracene (e.g., Suzuki coupling reaction, amine reaction). The production method can be represented by the following reaction scheme A:

[Reaction scheme A]

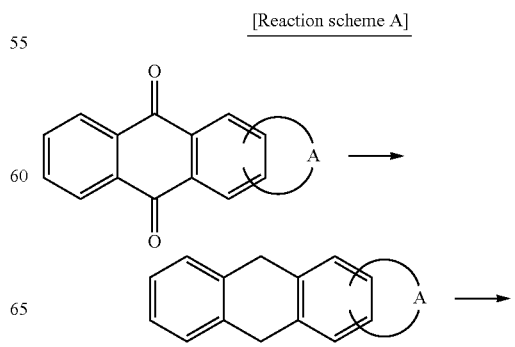

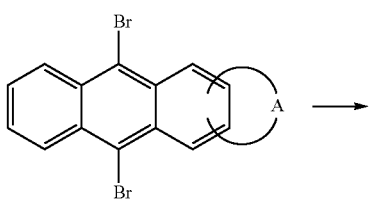
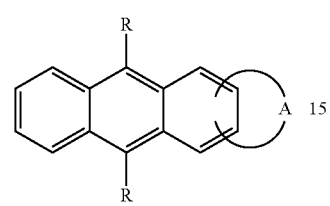
Specific examples of the compound represented by the formula (2) include, but are not limited to, the compounds represented by the following formulae (2-1) to (2-6):
(2-1)
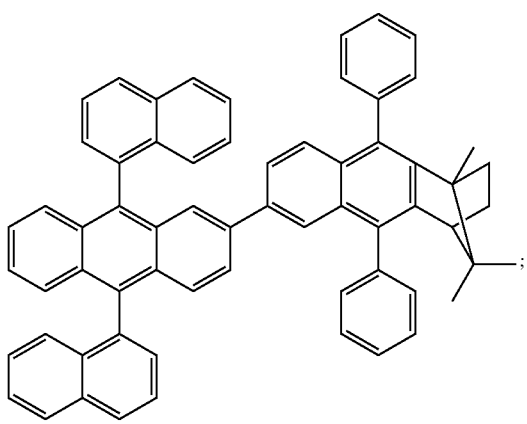
(2-2)
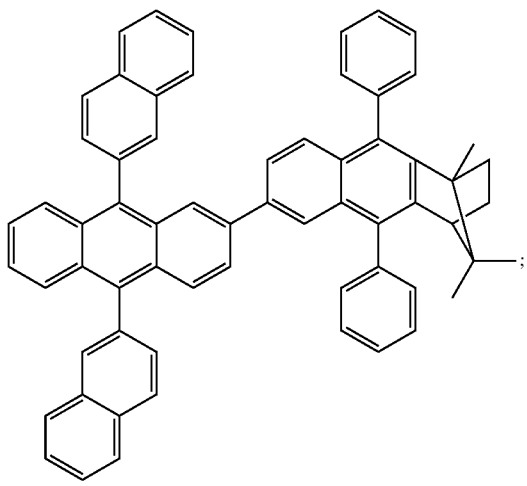
(2-3)
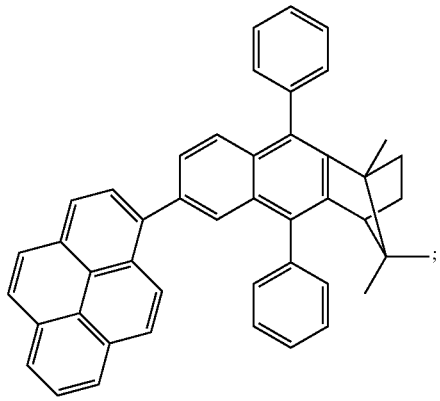
(2-4)
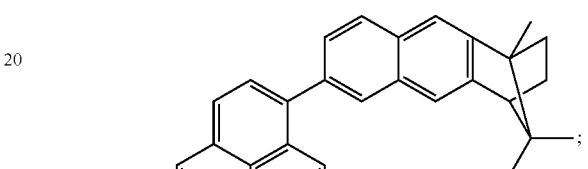
(2-5)
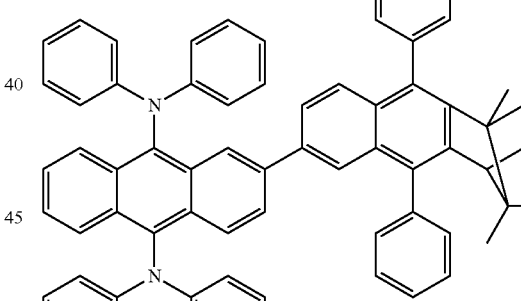
; and
(2-6)
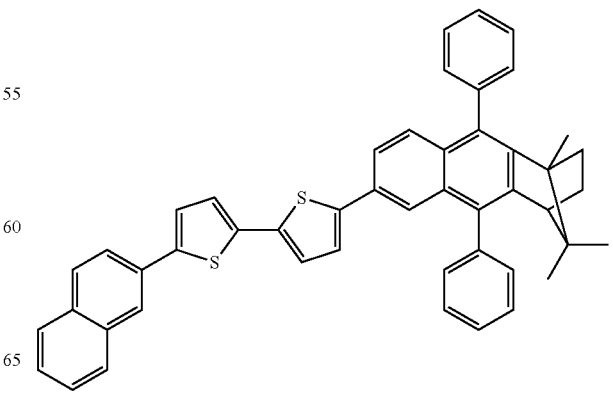

In an example of the general production method of the compound of the formula (2), the maximum number of the reaction site through a general fused cyclization can be 3 and various derivatives can be prepared by a general chemical reaction as in the formula (1). Specifically, various fused ring compounds can be synthesized by the introduction of various dichito (e.g., camphorquinone) derivatives as starting materials.

The production method can be represented by the following reaction scheme B:

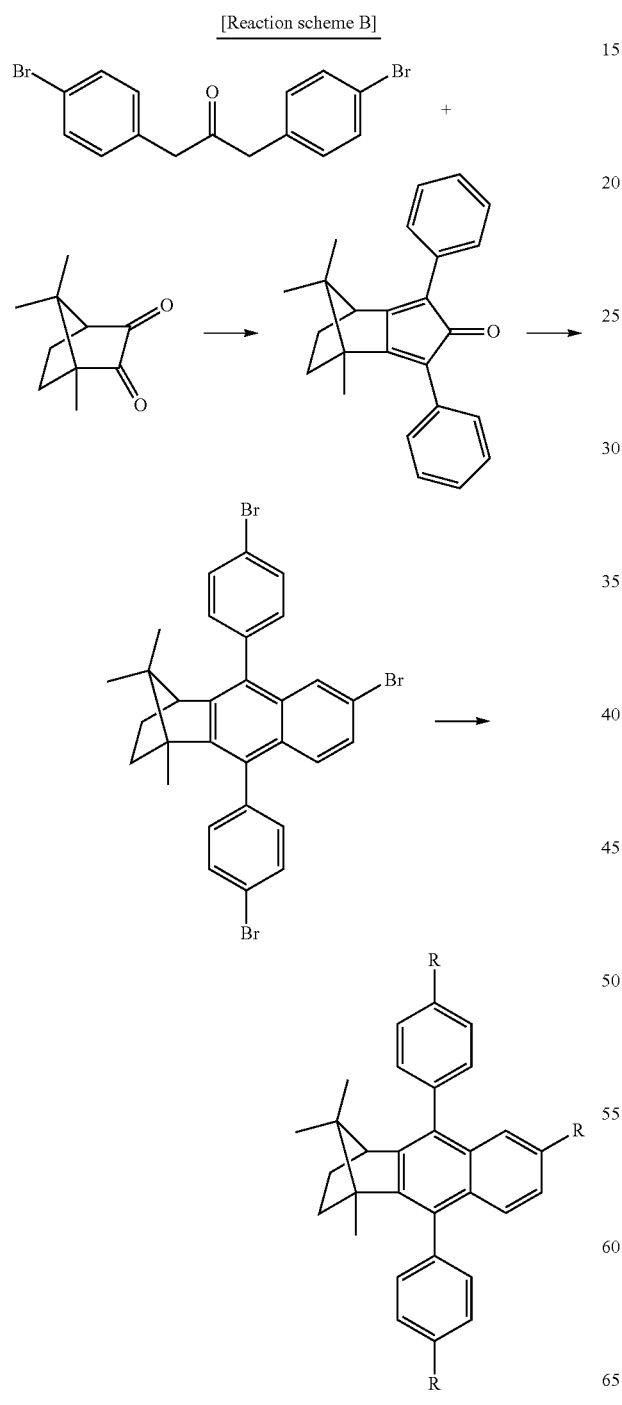

Specific examples of the compound represented by the formula (3) include, but are not limited to, the compounds represented by the following formulae (3-1) to (3-6):

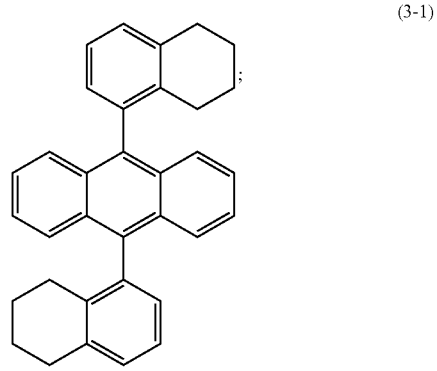

(3-1)

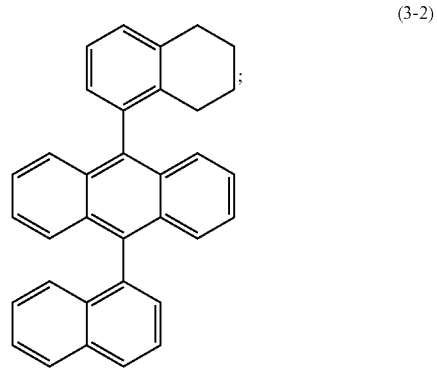

(3-2)

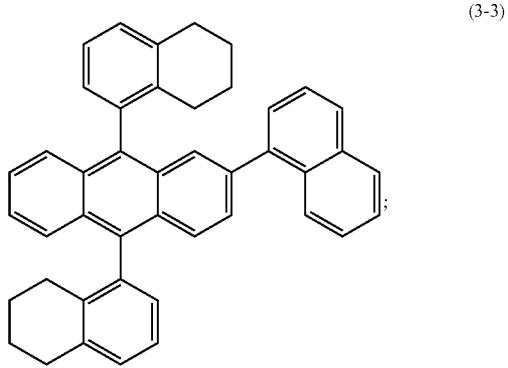

(3-3)

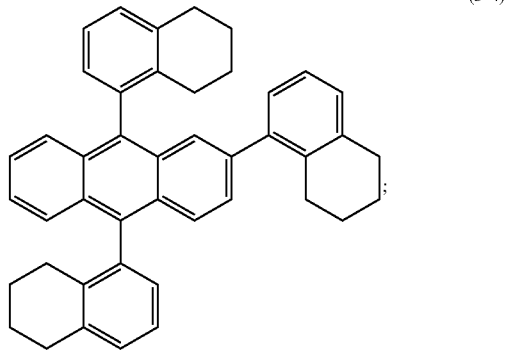

(3-4)

(3-5)

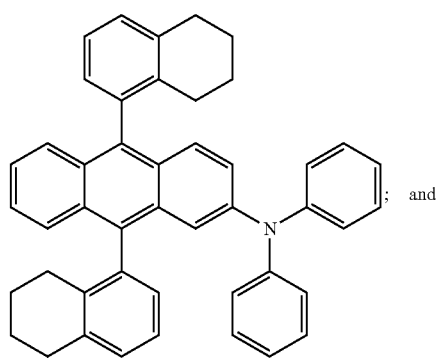

; and (3-6)

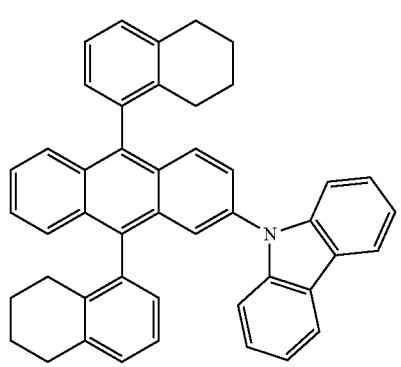

Further, the compounds of the formulae (1-7) and (1-8) can be included in the compound of the formula (3).

An example of the general production method of the compound of the formula (3) can be represented by the following reaction scheme C. In this case, when a halogen derivative including bromine is used instead of anthraquinone, the compound of the formula (3) can be synthesized by the same synthesis method.

[Reaction scheme C]

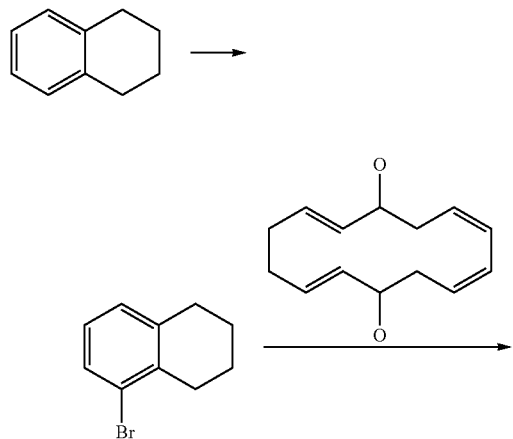

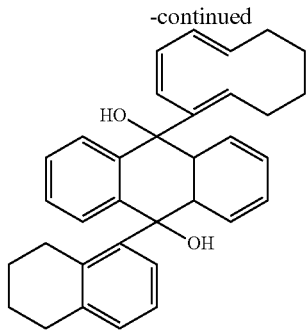

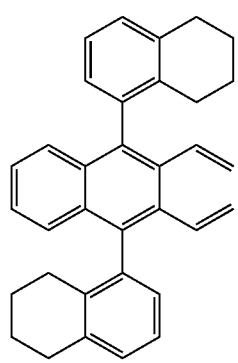

The production method of the compounds of the formulae (1), (2) and (3) will be explained in more detail in Preparative Examples to be described below.

On the other hand, the derivative that has the polycyclic aromatic hydrocarbon as a core, in which a substituted or unsubstituted $C_{2-30}$ cycloalkane, or a substituted or unsubstituted $C_{5-50}$ polycycloalkane is directly fused to the core or is fused to a substituent of the core, can carry out a function as a charge carrier extracting, injecting or transporting material. In this case, the charge carrier may be holes or electrons.

The organic electronic device requiring hole transportation between electrodes and an organic layer usually comprises two or more electrodes and one or more organic layer interposed therebetween. The organic electronic device can be largely classified into two types according to its operational principle as follows.

One type is an organic electronic device having a configuration in which an exciton is formed in an organic layer by energy flown from external energy into the device and the exciton is separated into an electron and a hole, the electron and the hole formed are used as a current source (voltage source). Examples of this type of the organic electronic device include an organic solar cell and a sensor such as an organic photoconductor (OPC).

The other type is an electronic device operated by a hole and/or electron directly injected into a semiconductive organic layer forming an interface with an electrode by applying a voltage to two or more electrodes. Examples of this type of the electronic device include an organic light emitting device carrying out light emission by simultaneously injecting an electron and a hole from two electrodes and an organic transistor having a switch function in which holes formed in an organic layer are transported from a source electrode (hereinafter referred to as a "source") to a drain electrode (hereinafter referred to as a "drain") by a voltage applied to a diode or gate.

In order to improve the device performance of the organic electronic device requiring hole transportation between the electrodes and the organic layer, it is important to enhance hole injection and extraction efficiency between the electrodes and the organic layer, and/or to efficiently transport holes formed in the organic layer to an electrode or other organic layers. To this end, the improvement in the device performance of most electronic devices has been attempted by forming at least one of an organic layer primarily required, which a main reaction takes place (for example, in the case of an organic solar cell, an organic layer forming an electron and a hole by photons from an external light source and in the case of an organic transistor, an organic layer forming a hole by a voltage applied to a gate), and an additional organic layer such as a charge injecting organic layer (hereinafter referred to as a "charge injecting layer"), a charge extracting organic layer (hereinafter referred to as a "charge extracting layer") and a charge transporting organic layer (hereinafter referred to as a "charge transporting layer").

Therefore, the charge carrier extracting, injecting or transporting material according to the invention can be used in an organic layer of an organic electronic device such as an organic light emitting diode, an organic solar cell, an organic transistor and an organic photoconductor (OPC).

In this case, according to the invention, the derivative that has the polycyclic aromatic hydrocarbon as a core, in which a substituted or unsubstituted $C_{2-30}$ cycloalkane, or a substituted or unsubstituted $C_{5-50}$ polycycloalkane is directly fused to the core or is fused to a substituent of the core, may be also mixed with 0.1 to 99.0% by weight of an inorganic metal, inorganic salt, or a different organic material.

Hereinafter, the organic light emitting device according to the invention will be described.

The organic light emitting device has a structure comprising a substrate, an anode, a cathode and at least one organic layer interposed between the anode and the cathode. The organic layers interposed between the anode and the cathode, can be further subdivided according to functions, if necessary, to thus increase the number of the organic layer, and to the contrary, one layer can has various functions to thus decrease the number of the organic layer.

Preferably, the organic light emitting device according to the invention may has a structure comprising a substrate, an anode, a hole injecting layer, a hole transporting layer, a light emitting layer, an electron transporting layer and a cathode, sequentially stacked from bottom to top in this order. Further, if desired, a hole blocking layer may be interposed between the electron transporting layer and the light emitting layer in order to prevent holes from moving into the electron transporting layer.

Figure 2:
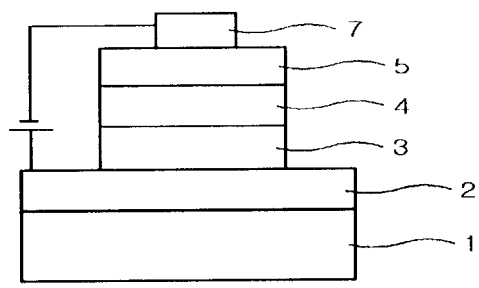
Figure 3:
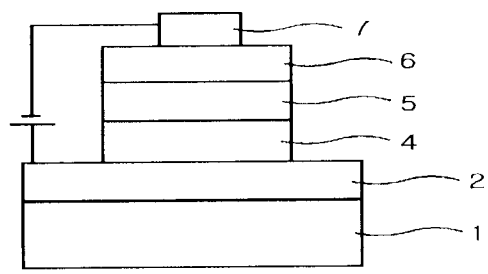
Figure 4:
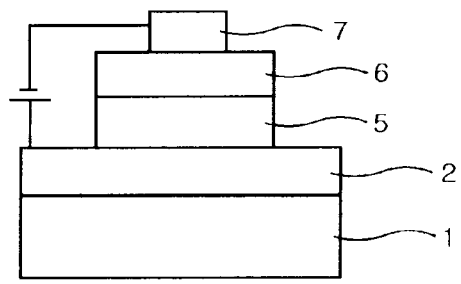
Figure 5:
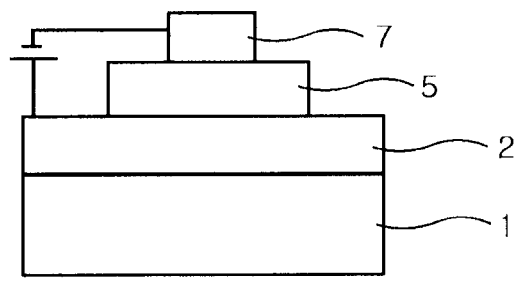

Examples of a structure of the organic light emitting device are shown in FIGS. 1 to 5, but are not limited thereto. In FIG. 1, the organic layers are divided into four portions. FIG. 2 shows an example of the light emitting layer simultaneously performing functions as the electron transporting layer and the light emitting layer. FIG. 3 shows an example of a hole transporting layer simultaneously performing functions of hole injection and hole transportation. FIG. 4 shows an example of a light emitting layer simultaneously performing three functions as a hole injecting layer, a hole transporting layer and a light emitting layer. FIG. 5 shows an example of a light emitting layer simultaneously performing functions as a hole injecting layer, a hole transporting layer, an electron transporting layer and a light emitting layer.

In the organic light emitting device according to the invention, each layer may be in the form of a thin film and the thin film may be formed by a conventional production method according to the materials used. For example, the thin film may be formed by CVD (chemical vapor deposition), EB (electron beam vapor deposition), thermal vapor deposition, sputtering, or thermal evaporation in high vacuum, or alternatively by spin-coating, roll-coating, screen-printing, dip-coating, doctor-blading, inkjet printing or thermal transfer after dissolving the derivative in a solution.

According to the invention, the derivative that has the polycyclic aromatic hydrocarbon as a core, in which a substituted or unsubstituted $C_{2-30}$ cycloalkane, or a substituted or unsubstituted $C_{5-50}$ polycycloalkane is directly fused to the core or is fused to a substituent of the core, may be used as a light emitting material in the organic light emitting device having the above-mentioned structure, or as a light emitting host or dopant for excited energy movement, for assisting light emission of other dopants. The polycyclic aromatic hydrocarbon derivative according to the invention may be used in combination of two or more types, and in combination with other light emitting dyes within the range of not damaging the performance of the invention.

When the polycyclic aromatic hydrocarbon derivative according to the invention is used as a dopant having an energy band gap smaller than a host forming a light emitting layer, the excitons generated on a host are transported to a dopant, thereby emitting light having high efficiency.

When the polycyclic aromatic hydrocarbon derivative according to the invention is used as a dopant, the derivative may be doped in the whole or part of the layer containing it, and may be doped uniformly or doped to have a concentration distribution in the direction of the film thickness thereof. The doping amount of the compound is preferably $10^{-3}$ to 15% by weight, more preferably 0.1 to 10% by weight relative to the host material.

Further, the polycyclic aromatic hydrocarbon derivative according to the invention may have, in addition to the above-mentioned light emitting properties, other properties necessary for an organic layer of an organic light emitting device, such as hole injecting, hole transporting, electron transporting and electron injecting properties.

The polycyclic aromatic hydrocarbon derivative according to the invention is preferably contained in a light emitting layer of an organic light emitting device. When a hole transporting layer and/or electron transporting layer have (has) a function as a light emitting layer without separately forming the light emitting layer, the derivative may be contained in the hole transporting layer and/or electron transporting layer.

The organic light emitting device comprising the polycyclic aromatic hydrocarbon derivative according to the invention can be enhanced in terms of the life span and the thermal stability. The reason is in that, by introducing a sterically bulky cycloalkyl group thereto, (1) a melting point and a glass transition temperature of the polycyclic aromatic hydrocarbon derivative can be increased to enhance thermal stability; and (2) by further exhibiting amorphous characteristics, a device can be prevented from breakdown that occurs due to crystallization caused by Joule heat generated upon operation of an organic light emitting device.

The following Preparative Examples and Examples are presented for the purpose of giving better understanding of the present invention. However, the following Preparative Examples and Examples are presented simply for the purpose of giving better understanding of the present invention, and thus the present invention is not limited thereto.

Preparative Example 1

Synthesis of Compound of Formula 1-1

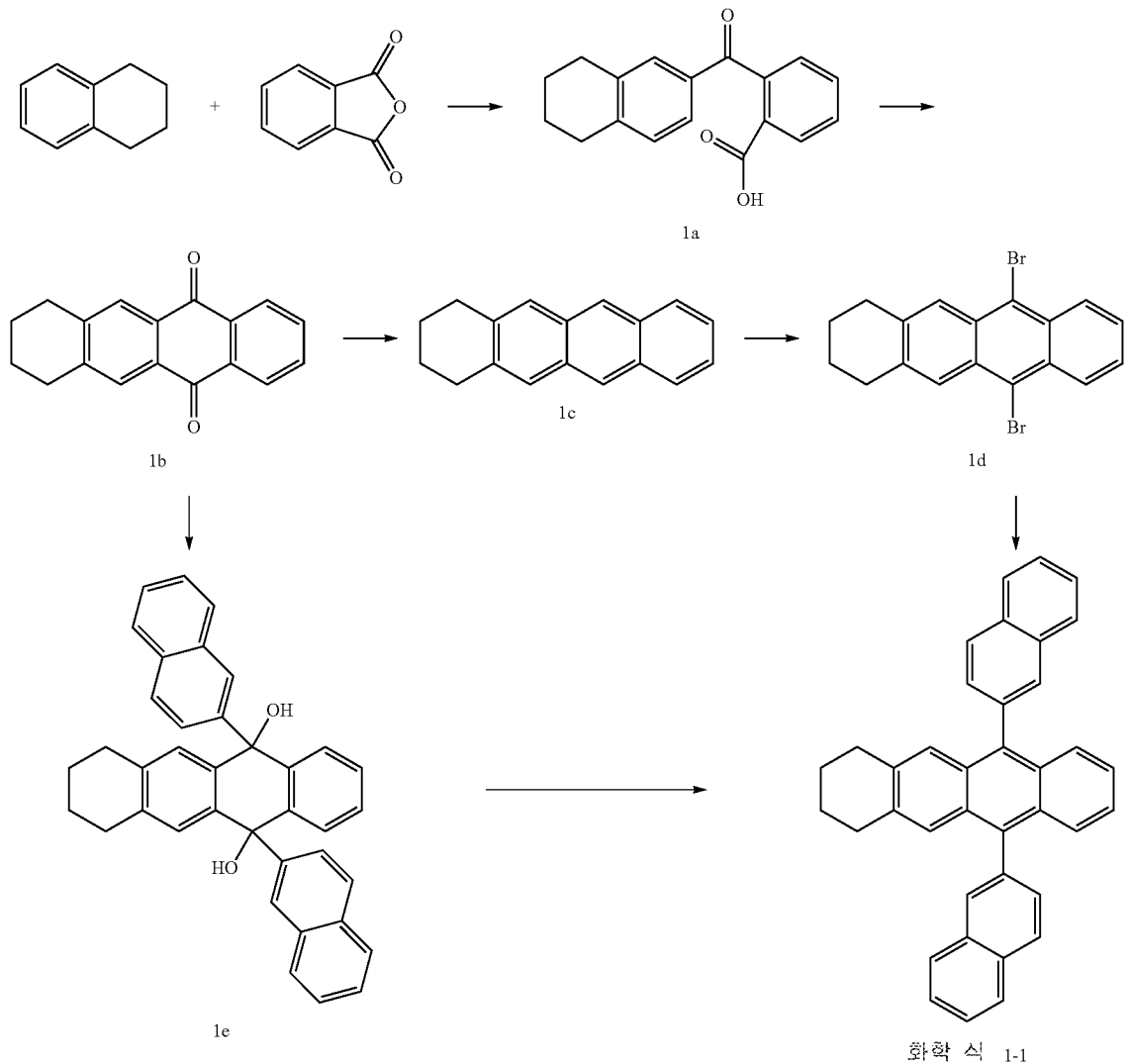

(1) Synthesis of Compound 1a

Tetralin (50.5 mL, 371 mmol) and phthalic anhydride (50.0 g, 338 mmol) were dissolved in dichloromethane (60 mL), AlCl$_3$ was slowly added thereto at 0° C., and the mixture was stirred at 0° C. for 30 minutes and was slowly warmed to normal temperature to proceed the reaction for 4 hours. The solution of the reaction mixture was poured into iced water, the organic phase was separated, and the water phase was twice extracted with dichloromethane. The organic phase was combined, dried on anhydrous MgSO$_4$, filtered, and then concentrated under reduced pressure. The residue was recrystallized from dichloromethane and petroleum ether to obtain a compound of Formula 1a (84 g, 89%).

MS [M+H] 281

(2) Synthesis of Compound 1b

Compound 1a (10 g, 35 mmol) was dissolved in dichloromethane (30 mL), and SOCl$_2$ (3.9 mL, 53.4 mmol) was added thereto to proceed the reaction for 12 hours. The reaction mixture was concentrated under reduced pressure to remove SOCl$_2$, and the residue was then dissolved in dichloromethane (30 mL). The solution was cooled to 0° C., AlCl$_3$ was slowly added thereto, and the mixture was warmed to normal temperature and then allowed to proceed the reaction for 3 hours. The reaction mixture was poured into iced water, the organic phase was separated, and the water phase was twice extracted with dichloromethane. The organic phase was combined, dried on anhydrous MgSO$_4$, filtered, and then concentrated under reduced pressure. The residue was purified by column chromatography to obtain Compound 1b (3.0 g, 32%).

MS [M+H] 262

(3) Synthesis of Compound 1c

Compound 1b (4.0 g, 15 mmol) was put to glacial acetic acid (250 mL), HI (40 mL) was slowly added thereto, and the mixture was refluxed for 8 hours. After termination of the reaction, the mixture was cooled to normal temperature, and the reaction mixture was poured into an aqueous sodium thiosulfate solution, and then extracted from ethyl ether. The organic phase was dried on anhydrous MgSO$_4$, filtered, and then concentrated under reduced pressure. The residue was purified by column chromatography to obtain Compound 1c (1.1 g, 31%).

MS [M+H] 233

(4) Synthesis of Compound 1d

Compound 1c (1.5 g, 6.4 mmol) was dissolved in DMF (30 mL), and NBS (N-bromosuccinimide) (2.87 g, 16.1 mmol) was added thereto to proceed the reaction for 10 hours. The reaction mixture was poured into water, and extracted from dichloromethane. The organic phase was dried on anhydrous MgSO$_4$, and then concentrated under reduced pressure. The residue was recrystallized from dichloromethane and ethanol to obtain Compound 1d (1.2 g, 47%).

MS [M] 390

(5) Synthesis of Compound of Formula 1-1

Compound 1d (1.3 g, 2.5 mmol) was dissolved in THF (tetrahydrofuran), 2-naphthyl boronic acid (0.9 g, 5.0 mmol) and 4 M K$_2$CO$_3$ (2.56 mL) were sequentially added thereto, and the mixture was refluxed. After termination of the reaction, the organic phase was separated and the water phase was extracted from ethyl acetate. The organic phase was combined, dried on anhydrous MgSO$_4$, filtered, and then concentrated under reduced pressure. The residue was purified by column chromatography and then recrystallized from ethyl acetate and ethanol to obtain a compound of Formula 1-1 (1.1 g, 87%).

1H NMR (500 MHz, CDCl$_3$) 8.08 (d, 2H), 8.05-8.02 (m, 2H), 7.98 (s, 2H), 7.96-7.92 (m, 2H), 7.68-7.58 (m, 8H), 7.42 (s, 2H), 7.25-7.22 (m, 2H), 2.81-2.76 (br, 4H), 1.78-1.73 (quintet, 4H); MS [M+H] 485

Preparative Example 2

Synthesis of Compound of Formula 1-2

The same procedure as in Preparative Example 1 was used until the step of synthesizing Compound 1d. Further, in the same manner as in Preparative Example 1 except that 1-naphthyl boronic acid was used instead of 2-naphthyl boronic acid in the step of synthesizing the compound of Formula 1-1 from Compound 1d, the compound of Formula 1-2 was synthesized.

1H NMR (500 MHz, CDCl$_3$) 8.12-8.02 (m, 4H), 7.78-7.72 (m, 2H), 7.68-7.62 (m, 2H), 7.55-7.48 (m, 2H), 7.39-7.35 (m, 2H), 7.3-7.18 (m, 6H), 7.14-7.11 (m, 2H), 2.72-2.62 (q, 4H), 1.74-1.64 (m, 4H); MS [M+H] 485

Preparative Example 3

Synthesis of Compound of Formula 2-1

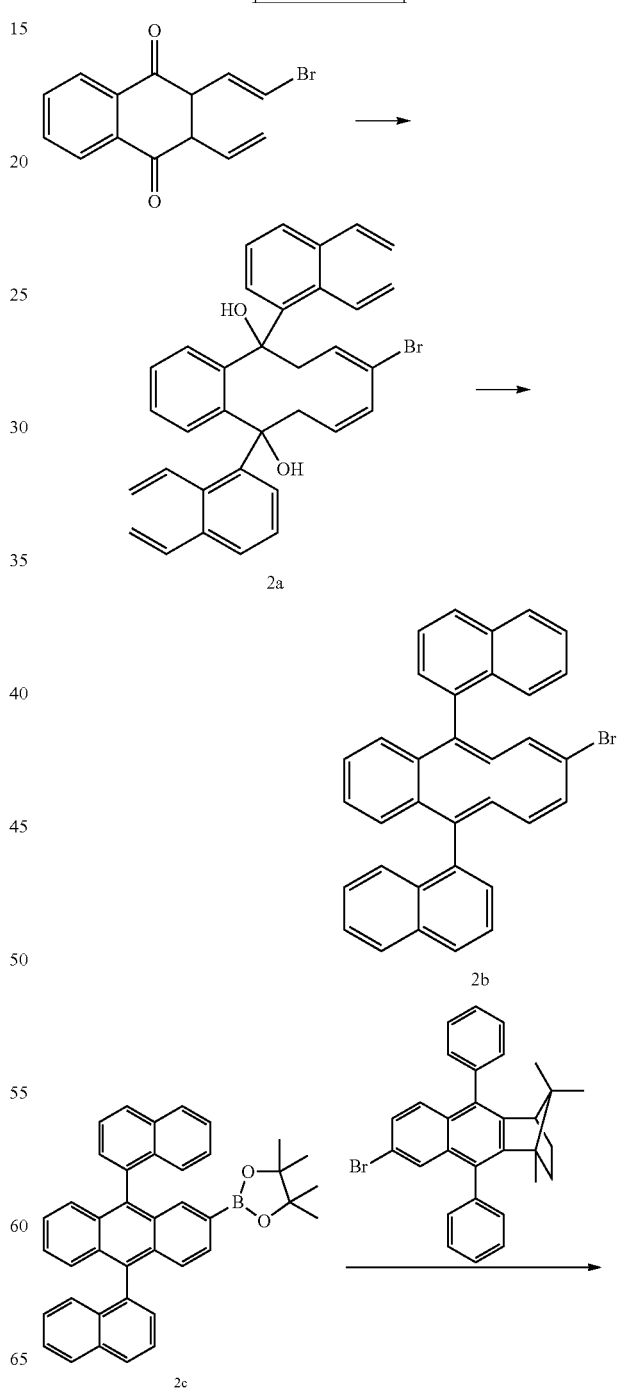

-continued

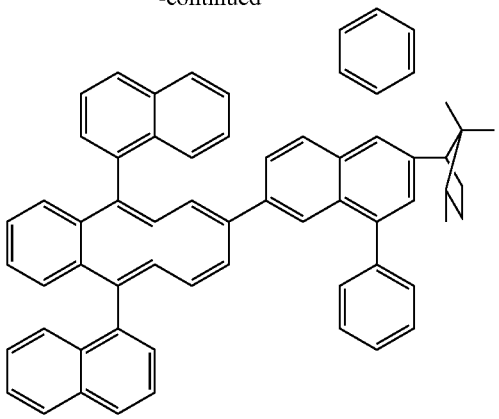

화학식 2-1

(1) Synthesis of Compound 2a (2-Bromo-9,10-di-naphthalen-1-yl-9,10-dihydro-anthracene-9,10-diol)

5-Bromo-1,2,3,4-tetrahydro-naphthalene (13.7 mL, 88.0 mmol) was dissolved in anhydrous THF (tetrahydrofuran) (100 mL), the solution was maintained at −78° C. with stirring, and n-BuLi (42.6 mL, 106 mmol) was slowly added dropwise to the solution. After 30 minutes, 2-bromo-9,10-anthraquinone (10.2 g, 35.5 mmol) was added thereto, and the mixture was stirred. After 2 hours, the reaction mixture was washed with a NH$_4$Cl solution, and further twice with distilled water, and then water was removed in anhydrous MgSO$_4$. The solvent was removed with a rotary evaporator. The residue was recrystallized from diethyl ether and petroleum ether to obtain Compound 2a (8.7 g, 45%). Analysis results of this compound are as follows.

1H NMR (500 MHz, CDCl$_3$) 7.78 (dd, 4H), 7.38 (dd, 4H), 6.82 (dd, 2H), 6.73 (dd, 2H), 6.46 (dd, 2H), 2.60 (t, 4H), 2.37 (t, 4H), 1.64 (m, 8H); MS [M+1-H2O] 526

(2) Synthesis of Compound 2b (2-Bromo-9,10-di-naphthalen-1-yl-anthracene)

2-Bromo-9,10-di-naphthalen-1-yl-9,10-dihydro-anthracene-9,10-diol (8.74 g, 16.1 mmol) was dissolved in glacial acetic acid (100 mL), the solution was stirred, KI (2.67 g, 16.1 mmol) and NaPO$_2$H$_2$ (17.1 g, 161 mmol) were added thereto, and the mixture was refluxed. As the reaction proceeded, the reactants started to be molten therein, and after 2 hours, white precipitates were generated to complete the reaction. Glacial acetic acid was filtered off, the precipitate was dispersed in ethanol, and H$_2$O was added thereto to generate the precipitates, which were further filtered to obtain a white solid compound 2b (7.5 g, 92%). Analysis results of this compound are as follows.
MS [M+1] 510

(3) Synthesis of Compound 2c (2-(9,10-Di-naphthalen-1-yl-anthracen-2-yl)-4,4,5,5-tetramethyl-[1,3,2]dioxaborolane)

Compound 2a (3 g, 5.9 mmol) was dissolved in anhydrous THF (tetrahydrofuran) (30 mL), the solution was maintained at −78° C. with stirring, and n-BuLi (3.1 mL, 7.7 mmol) was slowly added dropwise to the solution. After 30 minutes, 2-isopropoxy-4,4,5,5-tetramethyl-[1,3,2]dioxaborolane (1.6 mL, 7.7 mmol) was added thereto, and the mixture was stirred. After 1 hour, an aqueous NH$_4$Cl solution was added thereto, and the mixture was extracted from ethyl acetate, and further washed twice with distilled water, and then water was removed in anhydrous MgSO$_4$. The solvent was removed with a rotary evaporator. The residue was recrystallized from diethyl ether and petroleum ether to obtain Compound 2c (1.7 g, 52%).

(4) Synthesis of Compound of Formula 2-1

Compound 2c (1.7 g, 3.06 mmol) was dissolved in THF (20 mL), and Compound 3b (1.57 g, 3.36 mmol) was added to the solution. Pd(PPh$_3$)$_4$ (176 mg, 0.15 mmol), and an aqueous 2 M K$_2$CO$_3$ solution (6.12 mL, 12.2 mmol) were sequentially added thereto, and the mixture was refluxed with stirring. After 2 hours, THF (tetrahydrofuran) was added to the solution, and the mixture was extracted from ether, and further washed twice with distilled water. Water was removed from the solution in anhydrous MgSO$_4$. The solvent was removed with a rotary evaporator. The residue was purified by column chromatography to obtain a white solid. The solid was recrystallized from diethyl ether and petroleum ether and filtered under reduced pressure to obtain a white compound of Formula 2-1 (1.0 g, 39%).
MS [M+1] 817

Preparative Example 4

Synthesis of Compound of Formula 2-3

[Reaction scheme 3]

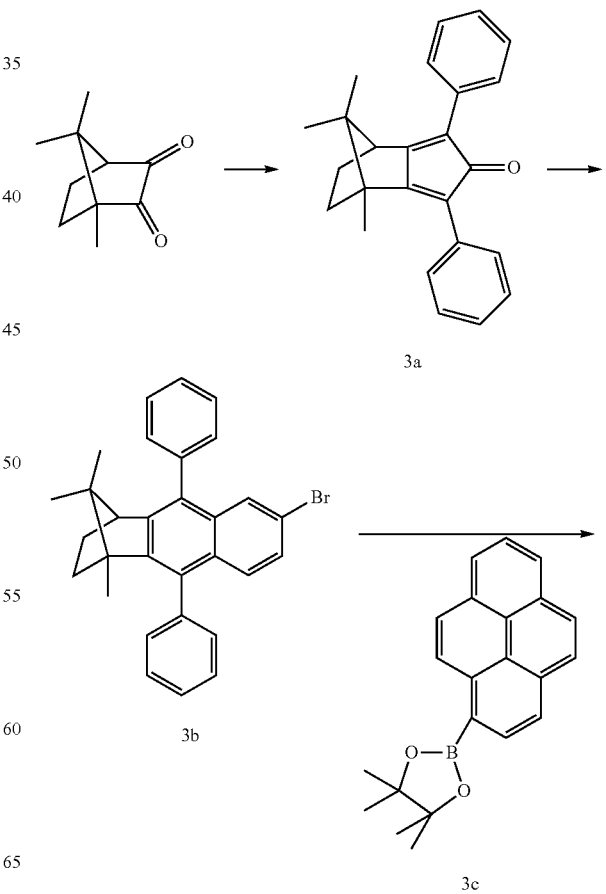

3a

3b

3c

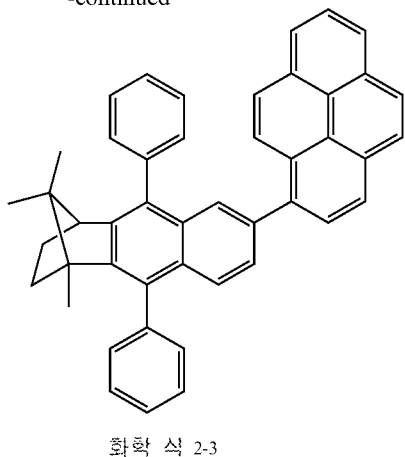

화학식 2-3

(1) Synthesis of Compound 3a (4,8,8-Trimethyl-1,3-diphenyl-4,5,6,7-tetrahydro-4,7-methano-inden-2-one)

DL-camphorquinone (10 g, 60 mmol) and diphenyl acetone (12.7 g, 60 mmol) were added to triethylene glycol (50 mL), the mixture was slightly heated to be molten, benzyl trimethylammonium hydroxide in methanol (40%) (6.5 mL, 14.3 mmol) was added thereto, and the mixture was heated to 120° C. and stirred. After the reaction proceeded, the mixture turned red, and after 24 hours and thus completion of the reaction, $H_2O$ was added thereto, and the mixture was extracted from ethyl acetate. Water was removed from the solution in anhydrous $MgSO_4$. The solvent was removed with a rotary evaporator. The residue was purified by column chromatography to obtain a red oily compound 3a (10 g, 49%).

MS [M+1] 341

(2) Synthesis of Compound 3b

Compound 3a (10 g, 29 mmol) and 5-bromoanthranilic acid (6.89 g, 31.9 mmol) were dissolved in 1,2-dichloroethane (100 mL), isoamyl nitrate (6.1 mL, 43.5 mmol) was added to the solution, and the mixture was refluxed at 90° C. After 1 hour, and thus completion of the reaction, $H_2O$ was added thereto, and the mixture was extracted from ethyl acetate. Water was removed from the solution in anhydrous $MgSO_4$. The solvent was removed with a rotary evaporator. The residue was purified by column chromatography to obtain a transparent oily compound 3b (6.7 g, 49%).

MS [M+1] 468

(3) Synthesis of Compound 3c (4,4,5,5-Tetramethyl-2-pyren-1-yl-[1,3,2]dioxaborolane)

2-Bromo-pyrene (5 g, 17.8 mmol) was dissolved in anhydrous THF (100 mL), the solution was maintained at −78° C. with stirring, and n-BuLi (9.7 mL, 23.2 mmol) was slowly added dropwise to the solution. After 30 minutes, 2-isopropoxy-4,4,5,5-tetramethyl-[1,3,2] dioxaborolane (4.8 mL, 23.1 mmol) was added thereto and the mixture was stirred. After 1 hour, an aqueous $NH_4Cl$ solution was added thereto, and the mixture was extracted from ethyl acetate, and further washed twice with distilled water, and then water was removed from the solution in anhydrous $MgSO_4$. The solvent was removed with a rotary evaporator to obtain a transparent oily mixed compound 3c (6.0 g, 99%).

MS [M+1] 329

(4) Synthesis of Compound of Formula 2-3

Compound 3c (2.4 g, 7.3 mmol) was dissolved in THF (30 mL), and Compound 3b (3.4 g, 7.3 mmol) was added to the solution. $Pd(PPh_3)_4$ (421 mg, 0.365 mmol) and an aqueous 2 M $K_2CO_3$ solution (14.6 mL, 29.2 mmol) were sequentially added thereto, and the mixture was refluxed with stirring. After 2 hours, THF was added to the solution, and the mixture was extracted from ether. Water was removed from the solution in anhydrous $MgSO_4$. The solvent was removed with a rotary evaporator. The residue was purified by column chromatography to obtain a white solid. The solid was recrystallized from methanol and $H_2O$, and filtered under reduced pressure to obtain a white Compound of Formula 2-3 (2.5 g, 58%).

MS [M+1] 589

Preparative Example 5

Synthesis of Compound of Formula 3-1

[Reaction scheme 4]

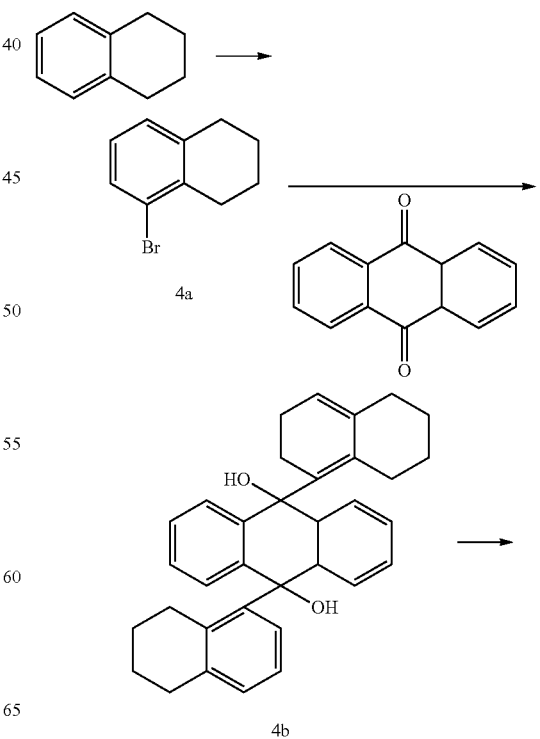

-continued

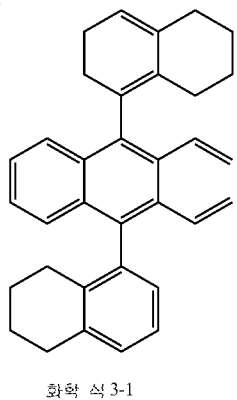

화학식 3-1

(1) Synthesis of Compound 4a
(5-Bromo-1,2,3,4-tetrahydro-naphthalene)

To one flask, alumina ($Al_2O_3$) (100 g) was added, and tetralin (13.2 g, 100 mmol) was slowly added dropwise for adsorption. To the other flask, alumina (100 g) was added, and bromine (5.17 mL, 100 mmol) was slowly added dropwise with stirring for adsorption. The flask having tetralin adsorbed thereon was put into an ice-bath at 0° C., and alumina having bromine adsorbed thereon was slowly added thereto with stirring while maintaining the temperature. As the reddish brown color of bromine disappeared, the reaction proceeded rapidly. The mixture was immediately separated by flash column chromatography to obtain a transparent oily compound 4a (11.5 g, 54.0%).

1H NMR (500 MHz, $CDCl_3$) 7.08 (m, 1H), 7.05 (m, 1H), 7.03 (m, 1H), 2.75 (m, 4H), 1.78 (m, 4H); MS [M+1] 212

(2) Synthesis of Compound 4b (9,10-Bis-(5,6,7,8-tetrahydro-naphthalen-1-yl)-9,10-dihydro-anthracene-9,10-diol)

Compound 4a (11.5 g, 54.4 mmol) was dissolved in anhydrous THF (100 mL), the solution was maintained at −78° C. with stirring, and then n-BuLi (30 mL, 65.1 mmol) was slowly added dropwise to the solution. After 30 minutes, 9,10-anthraquinone (3.77 g, 18.13 mmol) was added thereto and the mixture was stirred. After 1 hour, the reaction mixture was washed with a $NH_4Cl$ solution, and further twice with distilled water, and then water was removed from the solution in anhydrous $MgSO_4$. The solvent was removed with a rotary evaporator. The residue was purified by column chromatography to obtain Compound 4b (1.3 g, 15%).

1H NMR (500 MHz, $CDCl_3$) 7.78 (dd, 4H), 7.38 (dd, 4H), 6.82 (dd, 2H), 6.73 (dd, 2H), 6.46 (dd, 2H), 2.60 (t, 4H), 2.37 (t, 4H), 1.64 (m, 8H); MS [M+1-$H_2O$] 455

(3) Synthesis of Compound of Formula 3-1 (Aromatization of Compound 4b)

9,10-Bis-(5,6,7,8-tetrahydro-naphthalen-1-yl)-9,10-dihydro-anthracene-9,10-diol (Compound 4b) (1.3 g, 2.7 mmol) was dissolved in glacial acetic acid (30 mL), the solution was stirred, KI (448 mg, 2.70 mmol) and $NaPO_2H_2$ (2.86 g, 27.0 mmol) were added thereto, and the mixture was refluxed. As the reaction proceeded, the reactants started to be molten therein. After about 1 hour, white precipitates were generated to complete the reaction. Glacial acetic acid was filtered off, the precipitate was dispersed in ethanol, and $H_2O$ was added thereto to generate a precipitate, which was further filtered. Thus obtained white solid was separated by column chromatography to obtain a white solid compound of Formula 3-1 (0.47 g, 40%).

Melting point 388° C.; $^1H$ NMR (500 MHz, $CDCl_3$) 7.76 (dd, 4H), 7.30 (dd, 4H), 7.27 (d, 4H), 7.17 (m, 4H), 2.94 (t, 4H), 2.86 (t, 4H), 1.92 (m, 8H); MS [M+1] 439

Preparative Example 6

Synthesis of Compound of Formula 3-2

[Reaction scheme 5]

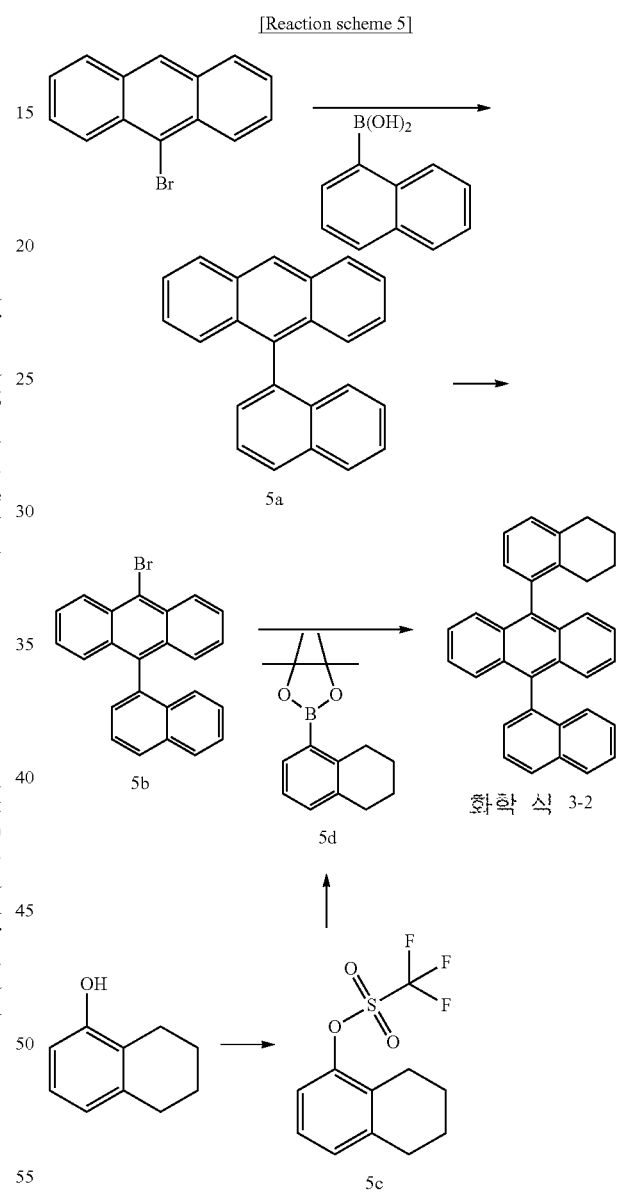

화학식 3-2

(1) Synthesis of Compound 5a
(9-Naphthalen-1-yl-anthracene)

9-Bromoanthracene (0.64 g, 2.50 mmol) was dissolved in THF, 1-naphthyl boronic acid (0.45 g, 2.50 mmol), and 4 M $K_2CO_3$ (2.56 mL) were sequentially added thereto, and the mixture was refluxed. After termination of the reaction, the organic phase was separated and the water phase was extracted from ethyl acetate. The organic phase was combined, dried on anhydrous $MgSO_4$, filtered, and then concentrated under reduced pressure. The residue was purified by column chromatography and then recrystallized from ethyl acetate and ethanol to obtain Compound 5a (0.64 g, 84.0%).

(2) Synthesis of Compound 5b (9-Bromo-10-naphthalen-1-yl-anthracene)

9-Naphthalen-1-yl-anthracene (2.3 g, 7.56 mmol) was dissolved in DMF (30 mL), and the solution was stirred. NBS (N-Bromosuccinimide) (1.48 g, 8.32 mmol) was added thereto, and the mixture was stirred. After 30 minutes, and thus completion of the reaction, water ($H_2O$) and a small amount of ethanol were added thereto to obtain a precipitate, which was filtered under reduced pressure to obtain an pale yellow compound 5b (2.6 g, 89%).

MS [M+H] 384

(3) Synthesis of Compound 5c (Trifluoro-methanesulfonic acid 5,6,7,8-tetrahydro-naphthalen-1-yl ester)

5,6,7,8-Tetrahydro-naphthalen-1-ol (10 g, 67.6 mmol) was added to dry pyridine (55 mL), and the mixture cooled with iced water with stirring. Triflic anhydride (13.6 mL, 81.1 mmol) was added thereto and the mixture was stirred. After 1 hour, water was added thereto, and the mixture was extracted from ethyl acetate. Water was removed from the solution in anhydrous $MgSO_4$. The solvent was removed with a rotary evaporator. The residue was separated by column chromatography to obtain a white oily compound 5c (18 g, 99%).

(4) Synthesis of Compound 5d (4,4,5,5-Tetramethyl-2-(5,6,7,8-tetrahydro-naphthalen-1-yl)-[1,3,2] dioxaborolane)

Compound 5c (19 g, 67.8 mmol) was dissolved in DMSO, and bis(pinacolato)diboron (18.9 g, 74.6 mmol) was added to the solution. $PdCl_2$ (dppf)/$CH_2Cl_2$ (2.97 g, 3.39 mmol), dppf (bis(diphenylphosphino)ferrocene) (1.88 g, 3.39 mmol), and KOAc (potassium acetate) (19.9 g, 203.4 mmol) were added thereto and the mixture was refluxed. After 3 hours, THF (tetrahydrofuran) and water were added thereto, and the mixture was extracted with ether. Water was removed from the solution in anhydrous $MgSO_4$, and the residue was treated with fuller's earth and filtered under reduced pressure. The solvent was removed with a rotary evaporator. The residue was separated by column chromatography to obtain an pale yellow oily compound 5d (10 g, 57%).

MS [M+1] 258

(5) Synthesis of Compound 3-2 (9-Naphthalen-1-yl-10-(5,6,7,8-tetrahydro-naphthalene-1-yl)-anthracene)

Compound 5b (1.5 g, 3.92 mmol) was dissolved in THF, and Compound 5d (5 g, 19.6 mmol) was added to the solution. Pd(PPh$_3$)$_4$ (226 mg, 0.196 mmol) and an aqueous 2 M $K_2CO_3$ solution (16 mL, 31.4 mmol) were sequentially added thereto, and the mixture was refluxed with stirring. After 2 hours, THF was added to the solution, and the mixture was extracted from ether. Water was removed from the solution in anhydrous $MgSO_4$, and the residue was treated with fuller's earth and filtered under reduced pressure. The solvent was removed with a rotary evaporator, the product was dispersed in EtOH, and $H_2O$ was added thereto to form a precipitate, which was further filtered to obtain a white solid compound of Formula 3-2 (1.1 g, 65%).

MS [M+1] 435

Preparative Example 7

Synthesis of Compound of Formula 3-3

[Reaction scheme 6]

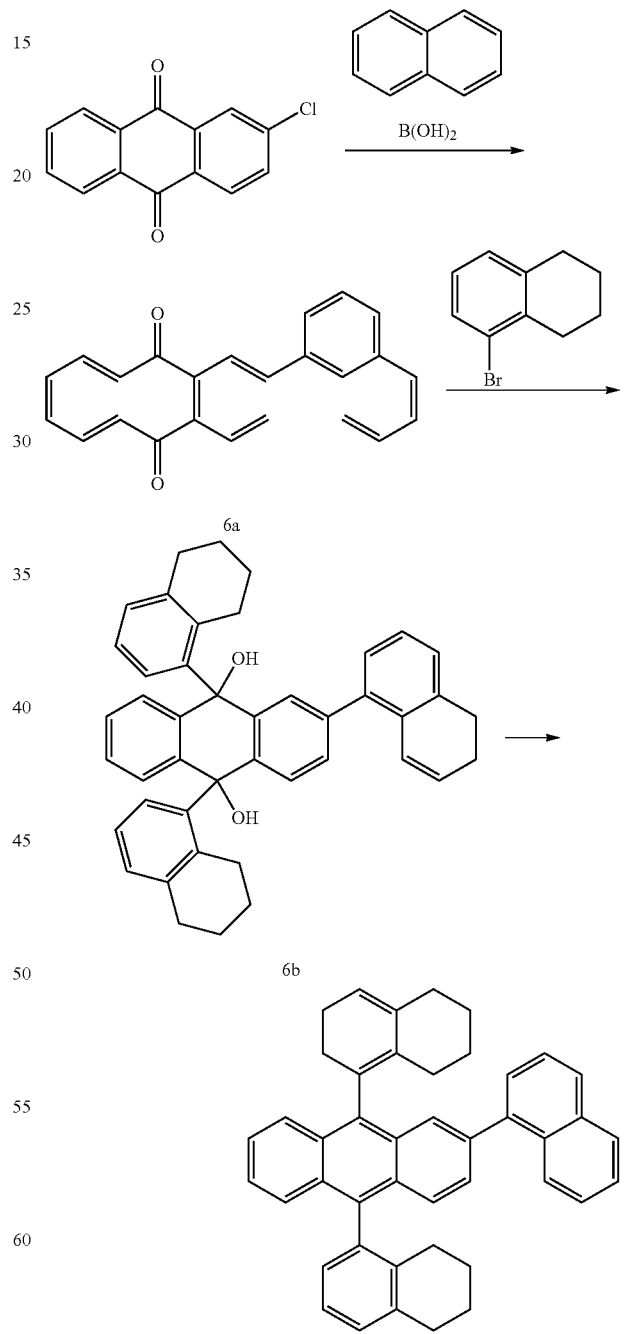

(1) Synthesis of Compound 6a (2-Naphthalen-1-yl-anthraquinone)

2-Chloro-anthraquinone (5.6 g, 23 mmol) was dissolved in THF (100 mL), 1-naphthyl boronic acid (5.15 g, 2.9 mmol) was added to the solution, $Pd(PPh_3)_4$ (1.33 g, 1.15 mmol) and an aqueous 2 M $K_2CO_3$ solution (92 mL, 184 mmol) were further added thereto, and the mixture was refluxed with stirring. After 2 hours, THF was added to the solution, and the mixture was extracted from ethyl acetate. Water was removed from the solution in anhydrous $MgSO_4$, and the residue was treated with fuller's earth, and filtered under reduced pressure. The solvent was removed with a rotary evaporator, and the product was recrystallized from ethyl ether and petroleum ether to obtain yellow solid Compound 6a (7.2 g, 94%).

MS [M+1] 335

(2) Synthesis of Compound 6b (2-Naphthalen-1-yl-9,10-bis-(5,6,7,8-tetrahydro-naphthalen-1-yl)-9,10-dihydro-anthracene-9,10-diol)

Compound 6a (1.6 g, 4.73 mmol) was dissolved in anhydrous THF (25 mL), the solution was maintained at −78° C. with stirring, and then n-BuLi (4.73 mL, 11.8 mmol) was slowly added dropwise to the solution. After 30 minutes, 5-bromo-1,2,3,4-tetrahydro-naphthalene (2.3 g, 10.8 mmol) was added thereto and the mixture was stirred. After 1 hour, the reaction mixture was washed with a $NH_4Cl$ solution, and further twice with distilled water, and then water was removed from the solution in anhydrous $MgSO_4$. The solvent was removed with a rotary evaporator. The residue was separated by column chromatography to obtain Compound 6b (1.6 g, 56%).

MS [M+1−$H_2O$] 581

(3) Synthesis of Compound 6c (2-Naphthalen-1-yl-9,10-bis-(5,6,7,8-tetrahydro-naphthalen-1-yl)-anthracene)

Compound 6b (1.6 g, 2.67 mmol) was dissolved in acetic acid (20 mL), the solution was stirred, KI (530 mg, 3.2 mmol) and $NaPO_2H_2$ (2.83 g, 26.7 mmol) were added thereto, and the mixture was refluxed. As the reaction proceeded, the reactants started to be molten therein, and after about 30 minutes, white precipitates were generated, thus leading to completion of the reaction. Glacial acetic acid was filtered off, the precipitate was dispersed in ethanol, and $H_2O$ was added thereto to generate a precipitate, which was further filtered to obtain a white solid compound of Formula 3-3 (1.0 g, 66%).

MS [M+1] 565

Preparative Example 8

Synthesis of Compound of Formula 3-4

[Reaction scheme 7]

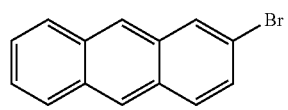

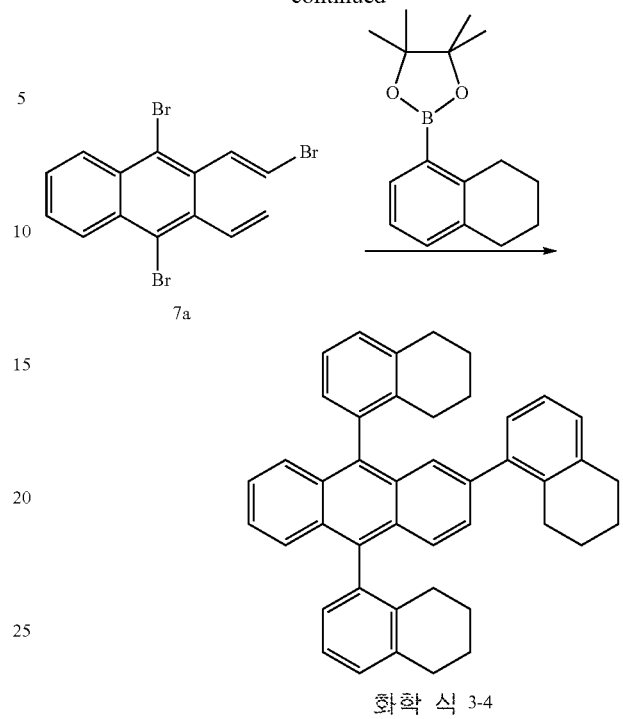

화학식 3-4

(1) Synthesis of Compound 7a (2,9,10-Tribromo-anthracene)

2-Bromo-anthracene (2 g, 7.78 mmol) was dissolved in DMF (30 mL), and the solution was stirred. NBS (N-Bromosuccinimide) (3.32 g, 18.7 mmol) was added thereto, and the mixture was stirred. After 30 minutes, and thus completion of the reaction, $H_2O$ and a small amount of EtOH were added thereto to obtain a precipitate, which was filtered under reduced pressure and dried in vacuo to obtain an pale yellow Compound 7a (3.0 g, 93%).

MS [M+1] 416

(2) Synthesis of Compound of Formula 3-4 (2,9,10-Tris-(5,6,7,8-tetrahydro-naphthalen-1-yl)-anthracene)

Compound 7a (3.0 g, 7.2 mmol) was dissolved in THF (30 mL), and Compound 5d (13 g, 50 mmol) was added to the solution. $Pd(PPh_3)_4$ (1.25 mg, 1.08 mmol) and an aqueous 2 M $K_2CO_3$ solution (28 mL, 57.6 mmol) were added thereto, and then the mixture was refluxed with stirring. After 2 hours, THF was added to the solution, and the mixture was extracted from ether. Water was removed from the solution in anhydrous $MgSO_4$, and the residue was treated with fuller's earth, and filtered under reduced pressure. The solvent was removed with a rotary evaporator, and the product was separated by column chromatography to obtain a white solid compound of Formula 3-4 (1.1 g, 27%).

MS [M+1] 569

Hereinbelow, Examples are presented, wherein the compounds prepared in the above Preparative Examples were applied in the organic light emitting devices.

Example 1

A glass substrate coated with the ITO (indium tin oxide) having a thickness of 1000 Å was ultrasonically washed in a distilled water in which a detergent was melted. The product manufactured by Fischer Co. was used as the detergent, and the distilled water was twice filtered with the filter manufactured by Millipore Co. After washing the glass substrate for 30 minutes, the glass substrate was further ultrasonically washed in the distilled water for 10 minutes, which was repeated twice. After washing, the glass substrate was sequentially ultrasonically washed in an isopropyl alcohol solvent, an acetone solvent, and a methanol solvent, dried, and then transported to a plasma cleaner.

Then, the substrate was washed for 5 minutes by using nitrogen plasma, and then transported to a vacuum deposition device.

Hexanitrile hexaazatriphenylene of the following Formula 4 was thermally vacuum deposited on the ITO transparent electrode to a thickness of 80 Å to form a hole injection layer.

[Formula 4]

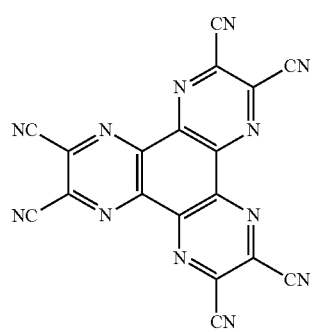

A layer (80 Å) formed of the compound of the following Formula 5, which is capable of injecting and transporting holes, was formed on the layer formed of the compound of the Formula 4 by vacuum deposition.

[Formula 5]

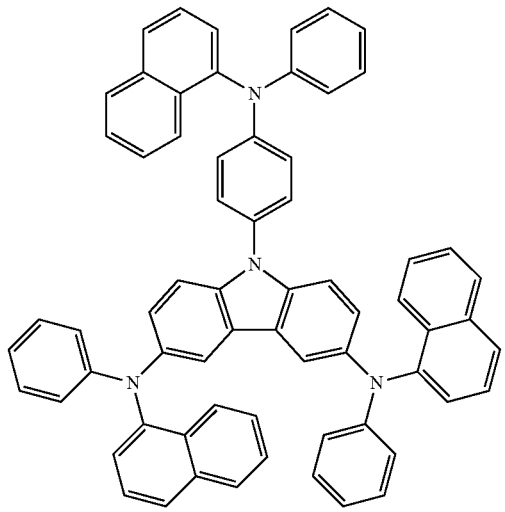

A layer (300 Å) formed of NPB of the following Formula 6, which is capable of transporting holes, was formed on the layer formed of the compound of the Formula 5 by vacuum deposition.

[Formula 6]

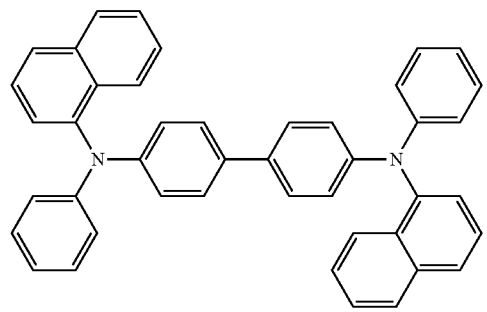

The compound of the Formula 7 as a green dopant was co-deposited at a concentration of 2% on the layer formed of the Formula 6 with the compound of the following Formula 1-1 as a light emitting host, to form a light emitting layer having a thickness of 300 Å.

[Formula 1-1]

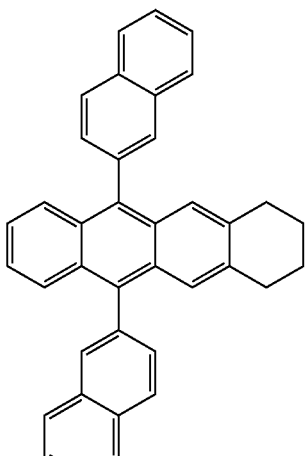

host

[Formula 7]

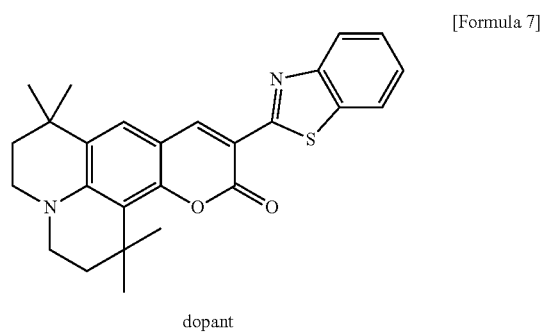

dopant

The compound of the following Formula 8, which is capable of injecting and transporting electron, was vacuum deposited on the light emitting layer to a thickness of 200 Å to complete the film formation of an organic layer.

[Formula 8]

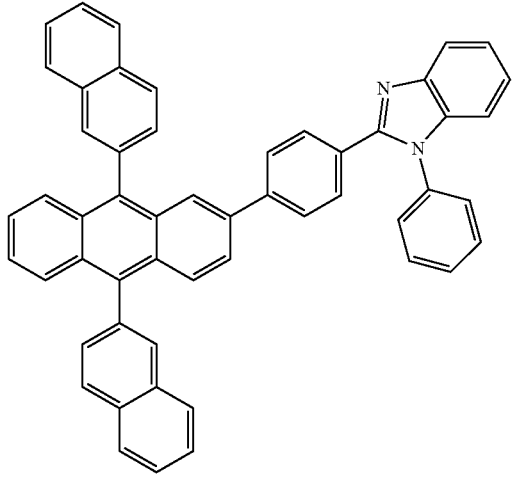

Lithium fluoride (LiF) having a thickness of about 12 Å and aluminum having a thickness of 2500 Å were sequentially vacuum deposited on the electron injecting and transporting layer to form a cathode. During the above step, the vacuum deposition rate of the organic compounds was maintained at 0.3 to 0.8 Å/sec, and the vacuum deposition rate of lithium fluoride and the vacuum deposition rate of aluminum were maintained at 0.3 Å/sec and 1.5 to 2.5 Å/sec, respectively.

100 mA/cm$^2$ of forward current was run on thus prepared organic light emitting device to form an electric field of 5.8 V. At this time, for emission color, a spectrum having a brightness of 6500 nit which corresponds to x=0.262 and y=0.590 based on a 1931 CIE color coordinate was observed. Upon application of a constant DC at a current density of 100 mA/cm$^2$, a time taken until the luminance was lowered to 50% of the initial luminance (L0.5) was 420 hours.

Examples 2 to 10

In the same manner as in Example 1 except that upon formation of the light emitting layer, the hosts and the dopants as described in Table 1 were used, organic light emitting devices were prepared. The results of the tests on the performances of the organic light emitting device as prepared in each of Examples are shown in Table 1.

Comparative Example 1

In the same manner as in Example 1 except that upon formation of the light emitting layer, 9,10-(2-naphthyl)anthracene was used as a host, an organic light emitting device was prepared.

TABLE 1

| Example | Host | Dopant (Concentration %) | Voltage * (V) | Emission color | Luminous sfficiency (cd/A) |
|---|---|---|---|---|---|
| Example 1 | Formula 1-1 | Formula 7(2%) | 5.8 | Green | 6.6 |
| Example 2 | Formula 1-1 | None | 6.0 | Blue | 1.7 |
| Example 3 | Formula 1-2 | Formula 7(2%) | 6.3 | Green | 6.5 |
| Example 4 | Formula 1-2 | None | 6.2 | Blue | 1.4 |
| Example 5 | Formula 2-2 | Formula 7(2%) | 6.9 | Green | 6.5 |
| Example 6 | Formula 2-2 | None | 6.8 | Blue | 1.9 |
| Example 7 | Formula 3-1 | Formula 7(2%) | 6.5 | Green | 6.8 |
| Example 8 | Formula 3-1 | None | 6.5 | Blue | 1.9 |
| Example 9 | Formula 3-2 | Formula 7(2%) | 6.2 | Green | 6.5 |
| Example 10 | Formula 3-2 | None | 6.4 | Blue | 1.8 |
| Comparative Example 1 | 9,10-(2-Naphthyl)anthracene | None | 6.5 | Blue | 1.2 |

* Voltage was measured at a current density of 100 mA/cm2.

As shown in Table 1, if the compound according to the present invention is applied to an organic light emitting device, it is possible to drive the device at low voltage and to enhance the life span.

The compound according to the present invention, to which various dopants are applied, can emit blue, green or red light, and in particular, provide a high efficiency light emitting material with excellent thermal stability. Further, the compound according to the present invention is used in the light emitting host in the organic light emitting device, it is possible to enhance the life span of the device and to drive the device at low voltage.

The invention claimed is:

1. An organic light emitting device comprising a first electrode, at least one organic layer, and a second electrode, laminated successively, wherein at least one layer of the organic layer comprises a compound selected from the group consisting of the compounds represented by the following formulae (3-2), (3-4), (3-5), and (3-6):

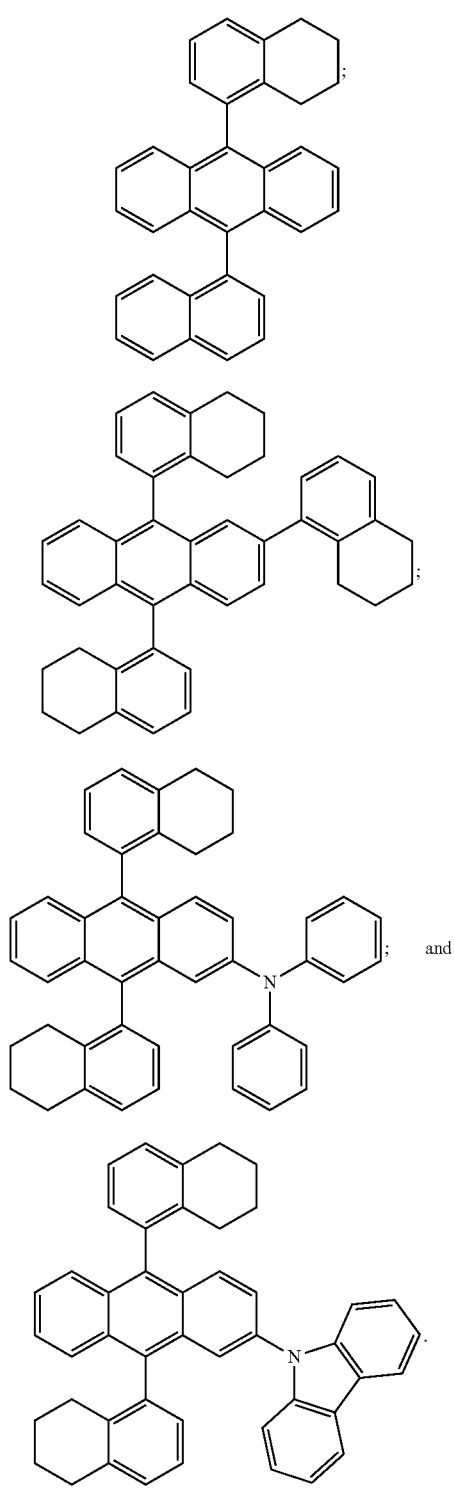

2. The organic light emitting device according to claim 1, wherein the organic layer containing the compound is mixed with 0.1 to 99.0% by weight of an inorganic metal, inorganic salt, or a different organic material.

3. A compound selected from the group consisting of the compounds represented by the following formulae (3-2), (3-4), (3-5), and (3-6):

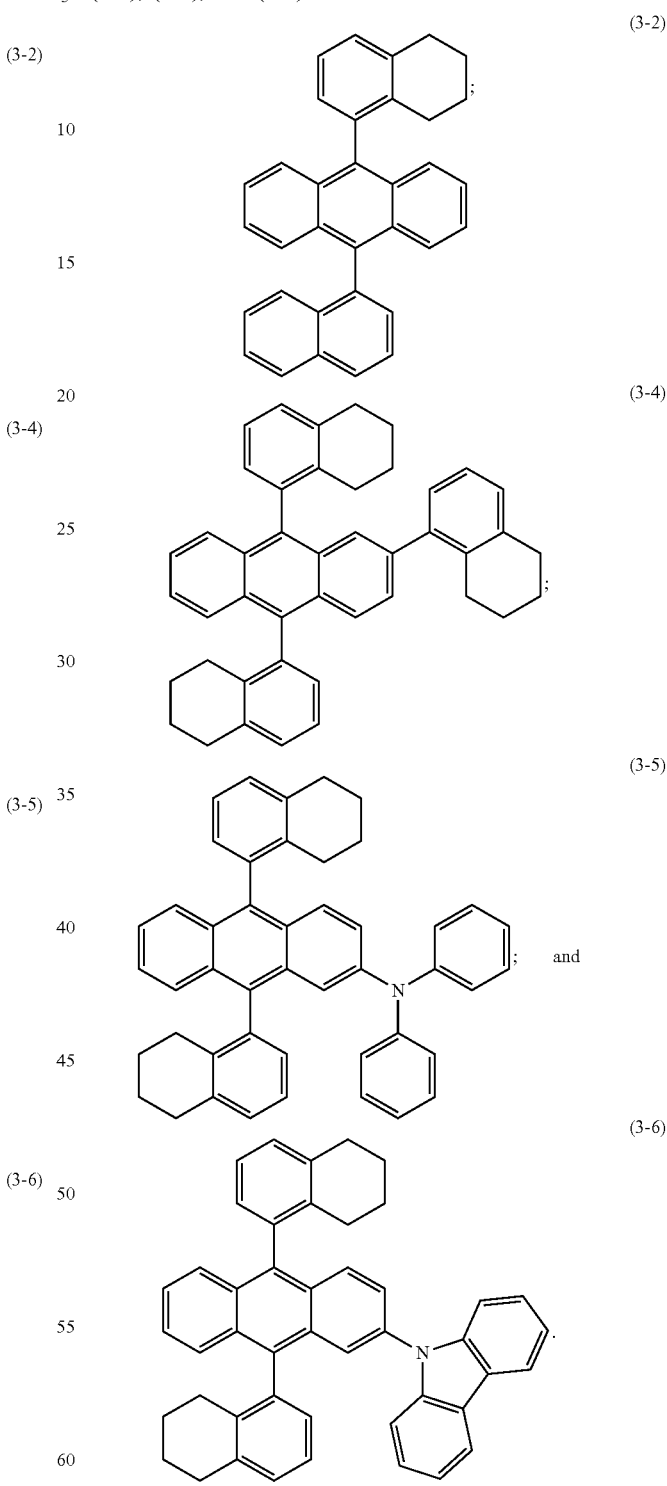

4. The compound according to claim 3, wherein the compound performs at least one of any functions among light emission, hole injection, hole transporting, and electron transporting in an organic electronic device.

* * * * *